United States Patent [19]

Carpino et al.

[11] Patent Number: 5,338,740
[45] Date of Patent: Aug. 16, 1994

[54] ANGIOTENSIN II RECEPTOR ANTAGONISTS

[75] Inventors: Philip C. Carpino, Mystic; Ronald T. Wester, Ledyard; Paul A. Da Silva Jardine, Mystic, all of Conn.

[73] Assignee: Pfizer Inc., New York, N.Y.

[21] Appl. No.: 91,099

[22] Filed: Jul. 13, 1993

[51] Int. Cl.$^5$ .................. A61K 31/435; C07D 471/04
[52] U.S. Cl. .................... 514/259; 514/299; 514/303; 514/333; 514/381; 514/386; 514/400; 544/244; 544/284; 544/287; 546/22; 546/23; 546/112; 546/118; 546/276; 546/278; 548/252; 548/253; 548/254; 548/300.7; 548/311.4; 548/312.1; 548/315.1; 548/334.5
[58] Field of Search ............ 546/118, 112, 22, 23, 546/276, 278; 544/244, 284, 287; 548/300.7, 311.4, 312.1, 315.1, 334.5, 252, 253, 254; 514/259, 299, 303, 333, 381, 386, 400

[56] References Cited

FOREIGN PATENT DOCUMENTS

| | | |
|---|---|---|
| 0253310 | 1/1988 | European Pat. Off. . |
| 0324377 | 7/1989 | European Pat. Off. . |
| 0399731 | 11/1990 | European Pat. Off. . |
| 0400974 | 12/1990 | European Pat. Off. . |
| 0407342 | 1/1991 | European Pat. Off. . |
| 0411766 | 2/1991 | European Pat. Off. . |
| 0420237 | 4/1991 | European Pat. Off. . |
| 0449699 | 10/1991 | European Pat. Off. . |
| 0450566 | 10/1991 | European Pat. Off. . |
| 0454511 | 10/1991 | European Pat. Off. . |
| 0465323 | 1/1992 | European Pat. Off. . |
| 0468372 | 1/1992 | European Pat. Off. . |
| 0480204 | 4/1992 | European Pat. Off. . |
| 0481448 | 4/1992 | European Pat. Off. . |
| 0489532 | 6/1992 | European Pat. Off. . |
| 0510812 | 10/1992 | European Pat. Off. . |
| 4032522 | 4/1992 | Fed. Rep. of Germany . |
| 9200977 | 1/1992 | PCT Int'l Appl. . |
| 9209278 | 6/1992 | PCT Int'l Appl. . |
| 9209600 | 6/1992 | PCT Int'l Appl. . |

OTHER PUBLICATIONS

Bühlmayer, Peter, "Angiotensin-II Antagonists: Patent Activity Since the Discovery of DuP-753," *Cardiovasculars*, pp. 1693-1718 (1992).

*Primary Examiner*—Bernard Dentz
*Attorney, Agent, or Firm*—Peter C. Richardson; Paul H. Ginsburg; Philip C. Strassburger

[57] ABSTRACT

The present invention relates to novel heterocyclic derivatives of the formula

Ar—W—Het wherein Ar, W and Het are as defined below, and related compounds, pharmaceutical compositions comprising such compounds, and the use of such compounds as regulators of the action of angiotensin II in mammals. The compounds of this invention are useful in the treatment and prevention of hypertension, glaucoma, renal disease, congestive heart failure, cognitive dysfunction, and other conditions in which the action of angiotensin II is implicated. This invention also relates to pharmaceutical compositions containing these compounds and to methods of inhibiting angiotensin II in mammals by administration of such compounds.

13 Claims, No Drawings

ANGIOTENSIN II RECEPTOR ANTAGONISTS

BACKGROUND OF THE INVENTION

The present invention relates to novel heterocyclic derivatives and related compounds, pharmaceutical compositions comprising such compounds, and the use of such compounds as regulators of the action of angiotensin II in mammals. The compounds of this invention are useful in the treatment and prevention of hypertension, glaucoma, renal disease, congestive heart failure, cognitive dysfunction, and other conditions in which the action of angiotensin II is implicated. This invention also relates to pharmaceutical compositions containing these compounds and to methods of inhibiting angiotensin II in mammals by administration of such compounds.

The renin-angiotensin system acts as a crucial regulatory mechanism in the control of homeostasis and fluid-/electrolyte balance in mammals, including humans. Renin-angiotensin system activity has a direct influence on blood pressure and has been found to play an important role in congestive heart failure and in the development and maintenance of hypertension. Angiotensin II, an octapeptide hormone produced via the cleavage of angiotensin I by angiotensin converting enzyme, is a potent and direct arterial vasoconstrictor which increases vascular resistance and blood pressure. Angiotensin II activity has also been implicated in the development of elevated intraocular pressure, for example, as caused by glaucoma, and it is known to stimulate the release of aldosterone resulting in vascular congestion and hypertension by promoting the retention of sodium and fluids. The present invention concerns regulation of the actions of angiotensin II which are mediated by the angiotensin II receptor.

Various heterocyclic compounds have been described as angiotensin II antagonists. Certain compounds referred to in the literature consist of a heterocyclic ring connected via a spacer group (i.e., a connecting group) to an aryl or heterocyclic ring substituted with an acidic moiety. In certain cases the spacer group consists of a methylene group connected to an aryl or heterocyclic group. Examples of such heterocycles in spacer groups include: imidazoles (EP 450566-A, published Oct. 9, 1991; EP 468372-A, published Jan. 29, 1992; DE 4010797), furans (EP 253310-A, published Jan. 20, 1988), thiophenes (EP 449699, published Oct. 2, 1991; EP465323-A, published Jan. 8, 1992; DE 4032522, published Apr. 16, 1992), pyrroles and pyridines (EP 480204, published Apr. 15, 1992), indoles (EP 489,532, published Jun. 10, 1992), benzofurans (WO 92 09278, published Jun. 11, 1992) and benzothiophenes (WO 92 09600, published Jun. 11, 1992). (All documents cited herein, including the foregoing, are incorporated herein in their entireties.)

SUMMARY OF THE INVENTION

The present invention relates to compounds in which a heterocyclic ring (hereinafter referred to as "Het")is connected to an aryl or thienyl group (hereinafter referred to as "Ar") via a carbobicyclic or heterobicyclic spacer group (hereinafter referred to as "W").

Broadly, the present invention relates to a compound of the formula

Ar—W—Het wherein Ar is selected from the group consisting of

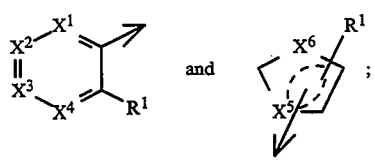

and $X^1$, $X^2$, $X^3$ and $X^4$ are independently selected from $CR^2$ and nitrogen;

one of $X^5$ and $X^6$ is CH and the other is S;

$R^1$ is selected from the group consisting of $CO_2H$, $NHSO_2CF_3$, $CONHSO_2(C_1-C_8)$alkyl, $PO_3H$, $SO_3H$, $-CONHSO_2(C_6H_5)$, $CONHSO_2CF_3$, tetrazole,

and $-SO_2NHCO_2(C_1-C_8)$alkyl;

$R^2$ is selected from hydrogen, $(C_1-C_8)$alkyl, $(C_2-C_{10})$alkenyl, $(C_3-C_8)$cycloalkyl, halo, hydroxy, $-O-(C_1-C_6)$alkyl, $-S-(C_1-C_6)$alkyl, $-SO-(C_1-C_6)$alkyl, $-SO_2-(C_1-C_6)$alkyl, $-NR^3R^4$, and phenyl, wherein said phenyl is optionally mono-, di- or tri-substituted with substituents independently selected from hydrogen, $(C_1-C_8)$alkyl, $(C_2-C_{10})$alkenyl, $(C_3-C_8)$cycloalkyl, halo, $(C_1-C_6)$alkoxy, $-S-(C_1-C_6)$alkyl, $-SO-(C_1-C_6)$alkyl, $-SO_2-(C_1-C_6)$alkyl, $-O-(C_1-C_6)$alkyl, and $-NR^3R^4$;

$R^3$ and $R^4$ are independently selected from hydrogen, $(C_1-C_8)$alkyl, $(C_2-C_{10})$alkenyl and $(C_3-C_8)$cycloalkyl, or $R^3$ and $R^4$, together with the nitrogen to which they are attached, form a cyclic 5-7 membered saturated or partially saturated carbocyclic or heterocyclic ring with one or two heteroatoms independently selected from nitrogen, oxygen and sulfur; and the dotted line represents that the ring containing $X^5$ and $X^6$ is aromatic:

W is a carbobicyclic or heterobicyclic ring system having the formula

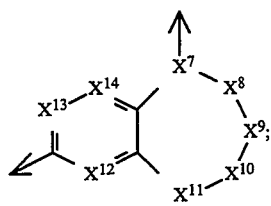

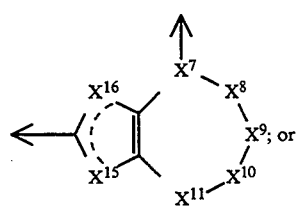

; or

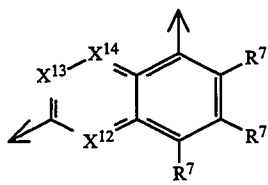

and $X^8$, $X^9$, $X^{10}$ and $X^{11}$ are present or absent, and each of $X^7$, $X^8$, $X^9$, $X^{10}$ and $X^{11}$ is independently selected from $CHR^5$, O, S, SO, $SO_2$, and $NR^6$;

$X^{12}$, $X^{13}$, and $X^{14}$ are independently selected from $CR^7$ or N;

$X^{15}$ and $X^{16}$ are independently selected from $CR^7$ and S;

$R^5$ is absent when the CH moiety of $CHR^5$ is connected to Het and when $R^5$ is present it is selected from hydrogen, $(C_1-C_8)$alkyl, $(C_2-C_{10})$alkenyl, $(C_3-C_8)$cycloalkyl, $-O-(C_1-C_6)$alkyl, and phenyl, wherein said phenyl is optionally mono-, di- or tri-substituted with substituents independently selected from hydrogen, $(C_1-C_8)$alkyl, $(C_2-C_{10})$alkenyl, $(C_3-C_8)$cycloalkyl, halo, $(C_1-C_6)$alkoxy, $-S-(C_1-C_6)$alkyl, $-SO-(C_1-C_6)$alkyl, $-SO_2-(C_1-C_6)$alkyl, $-O-(C_1-C_6)$alkyl, and $-NR^3R^4$;

$R^6$ is selected from $(C_1-C_8)$alkyl, $(C_3-C_8)$cycloalkyl and phenyl, wherein said cycloalkyl is saturated or partially saturated and wherein said cycloalkyl may optionally contain a heteroatom selected from nitrogen, oxygen, and sulfur, and said phenyl is optionally mono-, di- or tri-substituted with substituents independently selected from hydrogen, $(C_1-C_8)$alkyl, $(C_1-C_{10})$alkenyl, $(C_3-C_8)$cycloalkyl, halo, $(C_1-C_6)$alkoxy, $-S-(C_1-C_6)$alkyl, $-SO-(C_1-C_6)$alkyl, $-SO_2-(C_1-C_6)$alkyl, $-O-(C_1-C_6)$alkyl, and $-NR^3R^4$;

$R^7$ is selected from hydrogen, $(C_1-C_8)$alkyl, $(C_2-C_{10})$alkenyl, $(C_3-C_8)$cycloalkyl, halo, hydroxy, $-O-(C_1-C_6)$alkyl, $-S-(C_1-C_6)$alkyl, $-SO-(C_1-C_6)$alkyl, $-SO_2-2-(C_1-C_6)$alkyl, $-NR^3R^4$, and phenyl, wherein said phenyl is optionally mono-, di- or tri-substituted with substituents selected from hydrogen, $(C_1-C_8)$alkyl, $(C_1-C_{10})$alkenyl, $(C_3-C_8)$cycloalkyl, halo, $(C_1-C_6)$alkoxy, $-S-(C_1-C_6)$alkyl, $-SO-(C_1-C_6)$alkyl, $-SO_2-(C_1-C_6)$alkyl, $-O-(C_1-C_6)$alkyl, and $-NR^3R^4$; and the dotted line represents that the ring containing $X^{15}$ and $X^{16}$ contain one or two double bonds; and Het is selected from the group consisting of:

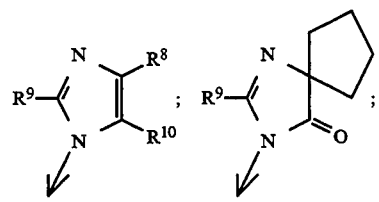

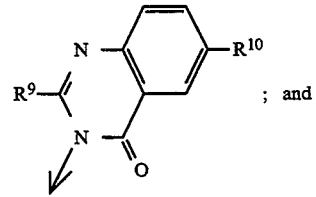

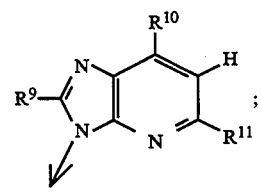

and $R^8$, $R^9$, $R^{10}$ and $R^{11}$ are independently selected from hydrogen, $(C_1-C_8)$alkyl, $(C_1-C_{10})$alkenyl, $(C_3-C_8)$cycloalkyl, halo, $(C_1-C_8)$alkoxy, $-S-(C_1-C_6)$alkyl, $-SO-(C_1-C_6)$alkyl, $-CO_2H$, $-SO_2NR^3R^4$, $-NR^3R^4$, and phenyl, wherein said phenyl is optionally mono-, di-, or tri-substituted with halo, hydroxy, nitro, $(C_1-C_8)$alkyl, $(C_3-C_6)$cycloalkyl, $(C_1-C_7)$alkoxy, $(C_1-C_7)$alkylthio, and amino, wherein said amino is optionally mono- or di-substituted with $(C_1-C_7)$alkyl;

and wherein each occurrence of $R^3$ can be the same or different from any other occurrence of $R^3$, and each occurrence of $R^4$ can be the same or different from any other occurrence of $R^4$;

with the proviso that: (a) no more than two of $X^1$, $X^2$, $X^3$ and $X^4$ can be nitrogen; and (b) at least two of $X^7$, $X^8$, $X^9$, $X^{10}$ and $X^{11}$ are present;

and to pharmaceutically acceptable salts thereof.

As used herein:

the term "halo," unless otherwise indicated, includes chloro, fluoro, bromo and iodo;

the term "alkyl", unless otherwise indicated, includes saturated monovalent hydrocarbon radicals having straight, branched or cyclic moieties or combinations thereof, for example methyl, ethyl, n-propyl, isopropyl, n-butyl, isobutyl and t-butyl;

the term "alkenyl," unless otherwise indicated, means straight or branched unsaturated hydrocarbon radicals, for example, ethenyl, 1- or 2-propenyl, 2-methyl-1propenyl and 1- or 2-butenyl;

the term "cycloalkyl," unless otherwise indicated, means a saturated carbocyclic radical, for example, cyclopropyl, cyclobutyl, cyclopentyl and cyclohexyl; and the term "alkoxy", unless otherwise indicated, includes O-alkyl groups wherein "alkyl" is defined as above.

Preferred compounds of the present invention include those wherein W has the formula

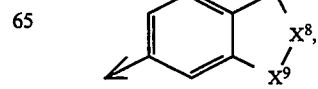

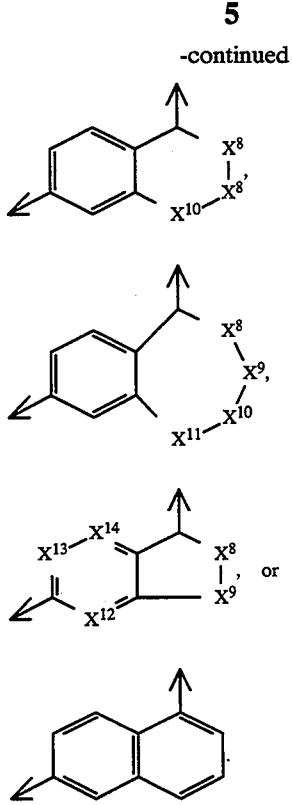

Examples of specific preferred compounds of the present invention are:

2-butyl-5-chloro-1-{5-[2-(1H-tetrazol-5-yl)-phenyl]-indan-1-yl}-1H-imidazole-4-carboxylic acid ethyl ester;
2-butyl-5-chloro-1-{5-[2-(1H-tetrazol-5-yl)-phenyl]-indan-1-yl}-1H-imidazole-4-carboxylic acid;
2-butyl-3-{5-[2-(1H-tetrazol-5-yl)-phenyl]-indan-1-yl}-1,3-diazaspiro[4.4]non-1-en-4-one;
(2-butyl-5-chloro-1-{5-[2-(1H-tetrazol-5-yl)-phenyl]-indan-1-yl}-1H-imidazol-4-yl)methanol
2-ethyl-5,7-dimethyl-3-{5-[2-(1H-tetrazol-5-yl)-phenyl]-indan-1-yl}-3H-imidazole[4,5-b]pyridine;
(S)-2-ethyl-5,7-dimethyl-3-{5-[2-(1H-tetrazol-5-yl)-phenyl]-indan-1-yl}-3H-imidazo[4,5-b]pyridine;
(R)-2-ethyl-5,7-dimethyl-3-{5-[2-(1H-tetrazol-5-yl)-phenyl]-indan-1-yl }-3H-imidazol[4,5-b]pyridine;
2-ethyl-7-methyl-3-{5-[2-(1H-tetrazol-5-yl)-phenyl}-indan-1-yl}-3H-imidazo[4,5-b]pyridine;
5,7-dimethyl-2-propyl-3-{5-[2-(1H-tetrazol-5-yl)-phenyl]-indan-1yl}-3H-imidazo[4,5-b]pyridine;
2-cyclopropyl-5,7-dimethyl-3-{5-[2-(1H-tetrazol-5-yl)-phenyl]-indan-1-yl}-3H-imidazo[4,5-b]pyridine;
2-butyl-5,7-dimethyl-3-{5-[2-(1H-tetrazol-5-yl)-phenyl]-indan-1-yl}-3H-imidazo[4,5-b]pyridine;
2-butyl-3-{5-[2-(1H-tetrazol-5-yl)-phenyl]-indan-1-yl}-3H-imidazo[4,5-b]pyridine;
2-[1-(2-ethyl-5,7-dimethyl-imidazo[4,5-b]pyridin-3-yl)-indan-5-yl-benzoic acid;
2-[5-(2-ethyl-5,7-dimethyl-imidazo[4,5-b]pyridin-3-yl)-5,6,7,8-tetrahydro-4H-naphthalen-2-yl]-benzoic acid;
2-ethyl-5,7-dimethyl-3-{6-[2-(1H-tetrazol-5-yl)-phenyl]-1,2,3,4-tetrahydro-4H-naphthalen-1-yl}-3H-imidazo[4,5-b]pyridine;
2-ethyl-5,7-dimethyl-3-{2-[2-(1H-tetrazol-5-yl)-phenyl]-6,7,8,9-tetrahydro-5H-benzocyclohepten-5-yl}-3H-imidazo[4,5-b]pyridine;
2-ethyl-5,7-dimethyl-3-{7-[2-(1H-tetrazol-5-yl)-phenyl]-chroman-4-yl}-3H-imidazo[4,5-b]pyridine;
2-ethyl-5,7-dimethyl-3-{3-[2-(1H-tetrazol-5-yl)-phenyl]-bicyclo[4.2.0]octa-1,3,5-trien-7-yl}-3H-imidazo[4,5-b]pyridine;
2-ethyl-5,7-dimethyl-3-{7-[2-(1H-tetrazol-5-yl)-phenyl]-chroman-4-yl}-3H-imidazo[4,5-b]pyridine;
2-ethyl-5,7-dimethyl-3-{3-[2-(1H-tetrazol-5-yl)-phenyl]-6,7-dihydro-5H-[1]pyridin-7-yl}-3H-imidazo[4,5-b]pyridine;
2-[5-(2-butyl-imidazo[4,5-b]pyridin-3-yl)-naphthalen-2-yl]-benzoic acid;
2-butyl-3-{6-[2-(1H-tetrazol-5-yl)-phenyl]-naphthalen-1-yl}3H-imidazo[4,5-b]pyridine; and
2-ethyl-5,7-dimethyl-3-{6-[2-(1H-tetrazol-5-yl)-phenyl-naphthalen-1-yl}-3H-imidazo[4,5-b]pyridine.

Other compounds of the present invention include the following:
2-ethyl-5,7-dimethyl-3-{7-[2-(2H-tetrazol-5-yl)-phenyl]-thiochroman-4-yl}-3H-imidazo[4,5-b]pyridine;
3-{1,1-dioxo-7-[2-(2H-tetrazol-5-yl)-phenyl]-thiochroman-4-yl}-2-ethyl-5,7-dimethyl-3H-imidazo[4,5-b]pyridine;
2-ethyl-5,7-dimethyl-3-{2-[2-(2H-tetrazol-5-yl)-phenyl]-5,6-dihydro-4H-thieno[2,3-b]thiopyran-4-yl}-3H-imidazo[4,5-b]pyridine;
2-ethyl-5,7-dimethyl-3-{2-[2-(2H-tetrazol-5-yl)-phenyl]-4,5,6,7-tetrahydrobenzo[b]thiophen-4-yl}-3H-imidazo[4,5-b]pyridine; P0 2-ethyl-5,7-dimethyl-3-{2-[2-(2H-tetrazol-5-yl)-phenyl]-5,6-dihydro-4H-cyclopenta[b]thiophen-4-yl}-3H-imidazo[4,5-b]pyridine;
2-ethyl-5,7-dimethyl-3-{6-[2-(2H-tetrazol-5-yl)-phenyl]-3,4-dihydro-2H-thieno[2,3-b]pyran-4-yl}-3H-imidazo[4,5-b]pyridine;
2-ethyl-5,7-dimethyl-3-{2-[2-(2H-tetrazol-5-yl)-phenyl]-6,7-dihydro-5H-[1]pyridin-5-yl}-3H-imidazo[4,5-b]pyridine;
5-(2 -ethyl-5,7 -dimethyl-imidazo[4,5-b]pyridin-3-yl )-2-[2-(2H-tetrazol-5-yl)-phenyl]-5,6,7,8-tetrahydro-quinoline;
4-(2ethyl-5,7-dimethyl-imidazo[4,5-b]pyridin-3-yl)-7-[2-(2H-tetrazol-5-yl)-phenyl]-3,4-dihydro-2H-thiopyrano[2,3-b]pyridine- 1,1 -dioxide;
2-ethyl-5,7-dimethyl-3-{2-[2-(2H-tetrazol-5-yl)-phenyl]-6,7-dihydro-5H-cyclopentapyrimidin-5-yl}-3H-imidazo[4,5-b]pyridine;
2-ethyl-5,7-dimethyl-3-{3-[2-(2H-tetrazol-5-yl)-phenyl]-6,7-dihydro-5H-[2]pyrindin-7-yl}-3H-imidazo[4,5-b]pyridine;
2-ethyl-5,7-dimethyl-3-{5-[3-(2H-tetrazol-5-yl)-thiophen-2-yl]-indan-1-yl}-3H-imidazo[4,5-b]pyridine;
2-ethyl-5,7-dimethyl-3-{5-[2-(2H-tetrazol-5-yl)-thiophen-3-yl]-indan-1-yl}-3H-imidazo[4,5-b]pyridine;
2-ethyl-5,7-dimethyl-3-{5-[4-(2H-tetrazol-5-yl)-thiophen-3-yl]-indan-1-yl}-3H-imidazo[4,5-b]pyridine;
2-ethyl-5,7-dimethyl-3-{5-[3-(2H-tetrazol-5-yl)-pyridin-4-yl]-indan-1-yl}-3H-imidazo[4,5-b]pyridine;
2-ethyl-5,7-dimethyl-3-{5-[4-( 2H-tetrazol-5-yl )-pyridin-3-yl]-indan-1-yl}-3H-imidazo[4,5-b]pyridine;
2-ethyl-5,7-dimethyl-3-{5-[3-(2H-tetrazol-5-yl)-pyridin-2-yl]-indan-1-yl}-3H-imidazo[4,5-b]pyridine;
(2-butyl-5-chloro-3-{5-[2-(2H-tetrazol-5-yl)-phenyl]-indan-1-yl}-3H-imidazole-4yl)methanol;
2-butyl-5-chloro-3-{5-[2-(2H-tetrazol-5-yl)-phenyl]-indan-1-yl}-3H-imidazole-4-carboxylic acid;

2-butyl-5-(1,1,2,2,2-pentafluoro-ethyl)-3-{5-[2-(2H-tetrazol-5-yl)-phenyl]-indan-1-yl}-3H-imidazole-4-carboxylic acid;

2-butyl-5-ethyl-3-{5-[2-(2H-tetrazol-5-yl)-phenyl]-indan-1-yl}-3H -imidazole-4-carboxylic acid;

2-ethoxy-3-{5-[2-(2H-tetrazol-5-yl)-phenyl]-indan-1-yl}-3H-benzoimidazole-4-carboxylic acid;

b   2-ethylsulfanyl-3-{5-[2-(2H-tetrazol-5-yl)-phenyl]-indan-1-yl}-3H-benzoimidazole-4-carboxylic acid;

N-benzoyl-2-[1-(2-ethyl-5,7-dimethyl-imidazo[4,5-b]pyridin-3-yl)-indan-5-yl]-benzenesulfonamide; and N-{2-[1-(2-ethyl-5,7-dimethyl-imidazo[4,5-b]pyridin-3-yl)-indan-5-yl]-phenyl}-benzenesulfonamide.

The present invention also relates to a pharmaceutical composition for treating or preventing a condition selected from the group consisting of hypertension, glaucoma, renal disease, congestive heart failure, and cognitive dysfunction in a mammal, including a human, comprising an amount of a compound of the formula Ar—W—Het, or a pharmaceutically acceptable salt thereof, effective in treating or preventing such condition, and a pharmaceutically acceptable carrier.

The present invention also relates to a method of treating or preventing a condition selected from the group consisting of hypertension, glaucoma, renal disease, congestive heart failure, and cognitive dysfunction in a mammal, including a human, comprising administering to said mammal an amount of a compound of the formula Ar—W—Het, or a pharmaceutically acceptable salt thereof, effective in treating or preventing such condition.

The present invention also relates to a pharmaceutical composition for antagonizing the effects of angiotensin II in a mammal, including a human, comprising an angiotensin II antagonizing amount of a compound of the formula Ar—W—Het, or a pharmaceutically acceptable salt thereof, and a pharmaceutically acceptable carrier.

The present invention also relates to a method of antagonizing the effects of angiotensin II in a mammal, including a human, comprising administering to said mammal an angiotensin II antagonizing amount of a compound of the formula Ar—W—Het, or a pharmaceutically acceptable salt thereof.

The present invention also relates to a pharmaceutical composition for treating or preventing a condition selected from the group consisting of hypertension, glaucoma, renal disease, congestive heart failure, and cognitive dysfunction in a mammal, including a human, comprising an amount of a compound of the formula Ar—W—Het, or a pharmaceutically acceptable salt thereof, effective in antagonizing the effect of angiotensin II at its receptor site, and a pharmaceutically acceptable carrier.

The present invention also relates to a method of treating or preventing a condition selected from the group consisting of hypertension, glaucoma, renal disease, congestive heart failure, and cognitive dysfunction in a mammal, including a human, comprising administering to said mammal an amount of a compound of the formula Ar—W—Het, or a pharmaceutically acceptable salt thereof, effective in antagonizing the effect of angiotensin II at its receptor site.

The present invention also relates to a pharmaceutical composition for treating or preventing a disorder in a mammal, including a human, the treatment or prevention of which is effected or facilitated by blocking the action of angiotensin II at its receptor, comprising an amount of a compound of the formula Ar—W—Het, or a pharmaceutically acceptable salt thereof, effective in antagonizing the effect of angiotensin II at its receptor site, and a pharmaceutically acceptable carrier.

The present invention also relates to a method of treating or preventing a disorder in mammal, including a human, the treatment or prevention of which is effected or facilitated by blocking the action of angiotensin II at its receptor, comprising administering to said mammal an amount of a compound of the formula Ar—W—Het, or a pharmaceutically acceptable salt thereof, effective in antagonizing the effect of angiotensin II at its receptor site.

The present invention also relates to a pharmaceutical composition for treating or preventing a disorder in a mammal, including a human, the treatment or prevention of which is effected or facilitated by blocking the action of angiotensin II at its receptor, comprising an amount of a compound of the formula Ar—W—Het, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by blocking the action of angiotensin II at its receptor, comprising administering to said mammal an amount of a compound of the formula Ar—W—Het, or a pharmaceutically acceptable salt thereof, effective in treating or preventing such disorder.

The compounds of the present invention have chiral centers and therefore exist in different enantiomeric forms. This invention relates to all optical isomers and all stereoisomers of compounds of the formula Ar—W—Het, and mixtures thereof.

Formula Ar—W—Het above includes compounds identical to those depicted but for the fact that one or more hydrogen or carbon atoms are replaced by radioactive isotopes thereof. Such radiolabelled compounds are useful as research and diagnostic tools in metabolism pharmokinetic studies and in binding assays. Specific applications in research include radioligand binding assays, autoradiography studies and in vivo binding studies, while specific applications in the diagnostic area include studies of the angiotensin II receptor in the human brain in in vivo binding in the relevant tissues for hypertension, e.g. immune-type cells or cells that are directly involved in reninangiotensin system activity and the like.

Also within the scope of this invention are the pharmaceutically acceptable salts of the compounds of this invention. The pharmaceutically acceptable acid salts are those formed from acids which form non-toxic acid salts, for example, hydrochloride, hydrobromide, sulfate, bisulfate, phosphate, acid phosphate, acetate, citrate, fumarate, gluconate, lactate, maleate, succinate, tartrate, methanesulfonate, benzenesulfonate, toluenesulfonate and formate salts. Pharmaceutically acceptable cationic salts include those non-toxic salts based on alkali and alkaline earth metals, for example, sodium, lithium, potassium, calcium and magnesium, as well as non-toxic ammonium, quaternary ammonium and amine cations, for example, ammonium, tetramethylammonium, methylamine, dimethylamine, trimethylamine, ethylamine, diethylamine and triethylamine.

DETAILED DESCRIPTION OF THE INVENTION

The compounds of formula Ar—W—Het may be prepared as described in the following reaction schemes and discussion. Unless otherwise indicated, Ar, W, Het, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $R^1$, $R^2$, $R^3$, $R^4$, $R^5$, $R^6$, $R^7$, $R^8$, $R^9$, $R^{10}$, and $R^{11}$ in the reaction schemes and discussion that follow are defined as above.

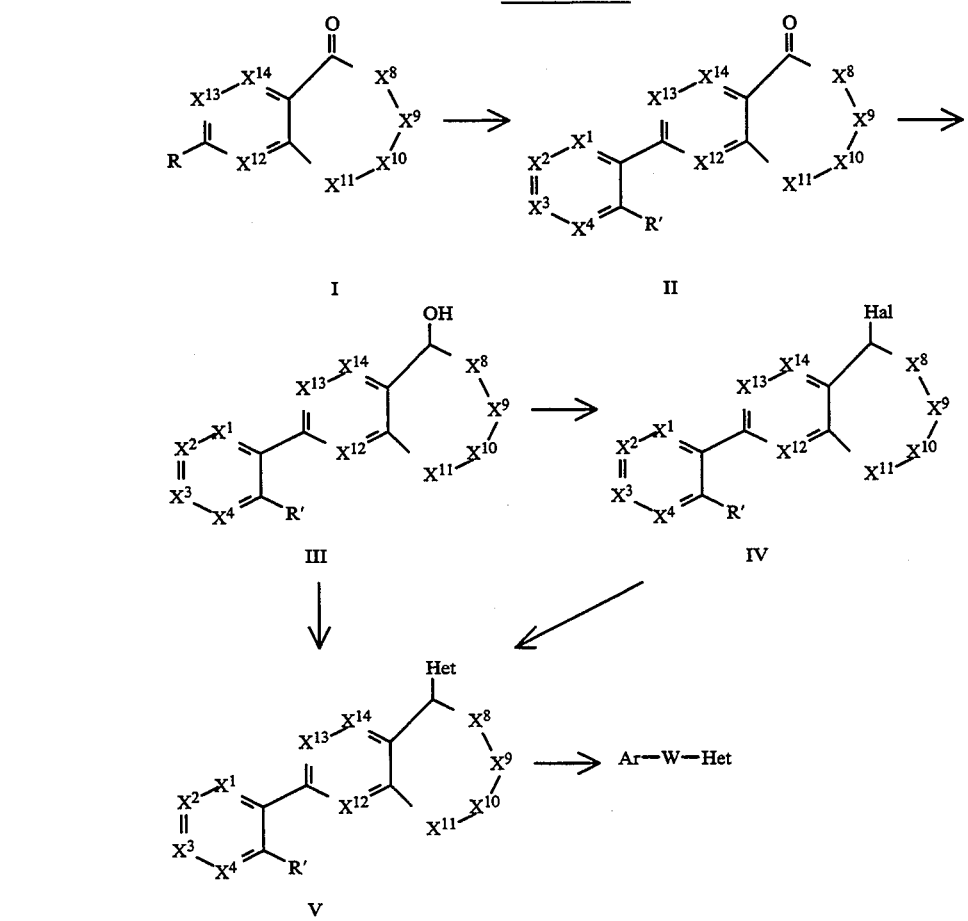

SCHEME I

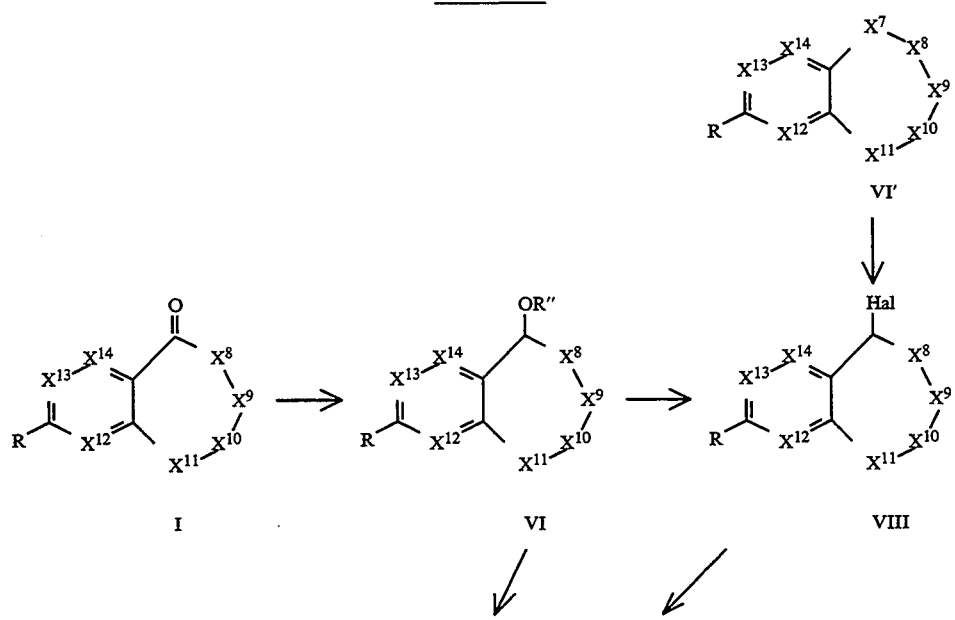

SCHEME II

SCHEME II

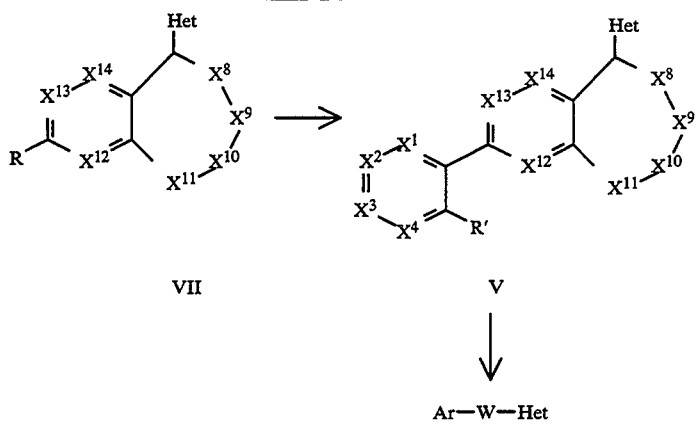

SCHEME III

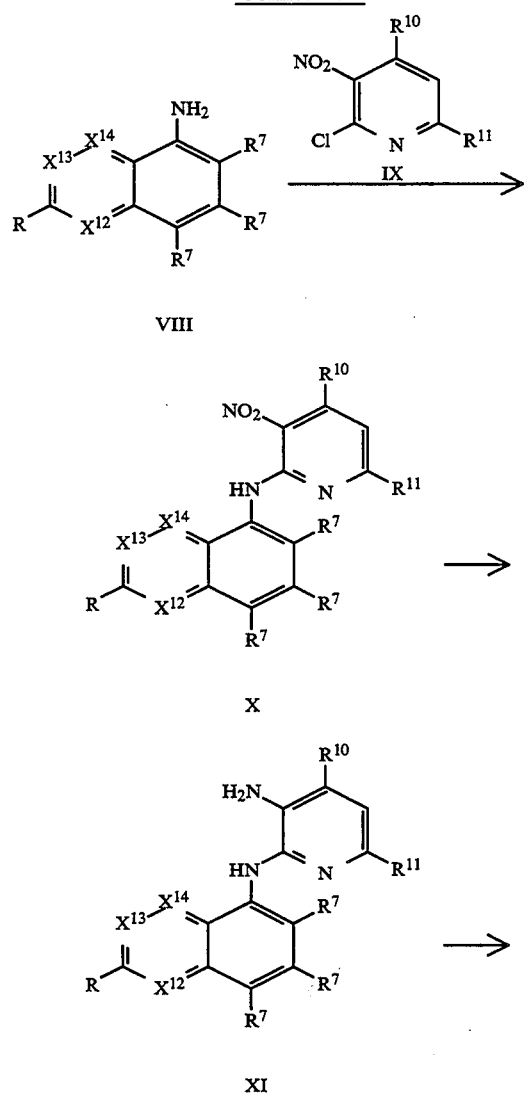

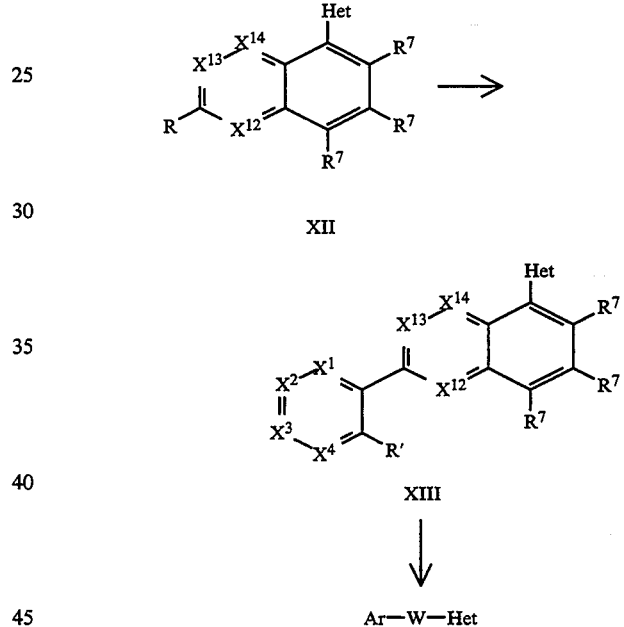

Schemes I–III illustrate several methods for preparing the compounds of the present invention. The compounds prepared by those methods may be purified by conventional techniques such as chromatography (flash column chromatography, medium pressure liquid chromatography, or high pressure liquid chromatography) and/or crystallization.

Scheme I illustrates the preparation of compounds of the present invention wherein W is a carbobicyclic ring. Treatment of the ketone I where R=bromine or iodine with hexaalkylditin and a palladium catalyst (preferably bis (triphenylphosphine) palladium (II) chloride (PdCl$_2$(PPh$_3$)$_2$)) gives I wherein R=((C$_1$-C$_8$)alkyl)$_3$Sn (alkyl stannane), which can be cross-coupled with a 2-haloaryl or a 2-halothienyl compound using a palladium catalyst (preferably PdCl$_2$(PPh$_3$)$_2$) in a solvent such as dimethylformamide (DMF), dioxane or dimethoxyethane (DME) at a temperature from 50° to 110° C. to give a compound of formula II (see, Stille, J. K.; Angew Int. Ed. Engl., 25, 508–524 (1986)). Where R=OH, compound I is first treated with triflic anhydride and a base (preferably pyridine or triethylamine)

in a chlorinated solvent such as methylene chloride, and then treated with lithium chloride (LiCl), hexaalkylditin and a palladium catalyst (preferably $PdCl_2(PPh_3)_2$) which gives the desired stannane which can be converted to compound II as described above (see, Echavarren, A. M. et al., J. Am. Chem. Soc., 109, 5478–5486,(1987)).

The biaryl ketone of formula II thus formed is reduced in a suitable solvent (preferably methanol) with a suitable reducing agent such as sodium borohydride at temperatures ranging from 0° C. to 23° C. to give the biaryl alcohol III. Compound III can be converted to the halide IV by treatment with thionyl chloride and a base such as pyridine in a chlorinated solvent such as methylene chloride at temperatures ranging from 0° C. to 23° C.

The alkylation of an alkali metal salt of a heterocycle (Het—prepared by literature methods listed below) with the halide IV gives the heterocyclic derivative V. The alkylation is generally carried out by treating the heterocycle with MH where M is lithium, sodium or potassium in an anhydrous solvent such as DMF, tetrahydrofuran (THF), DME, dimethylsulfoxide (DMSO) or dioxane, then adding the halide and heating the mixture for 24–48 hours at temperatures ranging from about 23° C. to about 145° C. of the solvent. Conversion of the compound of formula V into a compound of the present invention can be accomplished by standard methodologies. For V where $R' = CO_2CH_3$, saponification with a base preferably lithium hydroxide, potassium hydroxide or sodium hydroxide in a mixture of an alcoholic solvent and water at ambient temperature gives a compound of the present invention wherein $R^1=CO_2H$. For V where $R'=CN$, treatment with trimethyltin azide in a solvent such as toluene or xylene at reflux temperature for 5–24 hours gives a compound of the present invention wherein $R^1=CN_4H$. For V where $R'=SO_2NHC(C_6H_5)$, treatment with a mild acid, preferably acetic acid, in a solvent such as water gives the sulfonamide which can be acylated at room temperature with a suitable agent in the presence of a base preferably 4-N,N-dimethylaminopyridine (DMAP) in a chlorinated solvent such as methylene chloride to give a compound of the present invention wherein $R^1=SO_2NHCO(C_6H_5)$.

The heterocycles (Het) described in this scheme can be prepared by known methods as follows: imidazoles- EP 324377, published Jul. 19, 1989, and WO 92 00977, published Jan. 23, 1992; imidazolines- EP 454511 A1, published Oct. 30, 1991; benzimidazoles and imidazopyridines- EP-399731-A, published Nov. 28, 1990, EP-400974-A, published Dec.5, 1990, and EP-420237-A, published Apr.3, 1991; quinazolinones- EP-510812-A1, published Oct. 28, 1992; EP-481448-A, published Apr.22, 1992; EP-411766-A, published Feb.6, 1991; EP-44581-A and EP-407342-A, published Jan.9, 1991.

For the synthesis of enantiomerically pure derivatives of the present invention where Het is an imidazopyridine derivative, the biaryl ketone II can be reduced using borane-dimethylsulfide in an ethereal solvent such as THF and employing a chiral catalyst such as (S)-(—)-2-methyl-CBS-oxazaborolidine (see, Corey et al.; J. Am. Soc. Chem. 1987, 109, 5551–5553; Mathre et al.; J. Org. Chem. 58, 2880–2888 (1993)). The chiral alcohol III can be converted to V without racemization by using Mitsunobu chemistry (see Mitsunobu, O.; Synthesis, 1–28 (1981)). This reaction is generally carried out by adding a mixture of triphenylphosphine and dialkyldiazodicarboxylate in a non-polar solvent such as toluene to a slurry of the appropriate alcohol and imidazopyridine in the same solvent.

The compounds of the present invention can be prepared by the alternate route illustrated in Scheme II. Compound I, $R=OH$ can be acylated with a suitable agent in the presence of a base such as pyridine or DMAP to give I, $R=OCO(C_6H_5)$. Reduction of the ketone function with an agent such as sodium borohydride in an alcoholic solvent at temperatures ranging from 0° C. to 23° C. gives VI which, upon treatment with an acetylating agent such as acetyl chloride or acetic anhydride in the presence of a base such as pyridine or DMAP, gives VI, $R'=OCO(C_6H_5)$, $R''=OAc$. Treatment of VI with two equivalents of an alkali metal salt of a heterocycle (prepared by adding MH where M is lithium, sodium or potassium to the heterocycle)in a suitable solvent such as DMF, THF, DMSO or dioxane at ambient temperature gives VII, $R=OH$. Compound VII, $R=OH$ can be converted to the biaryl derivative of the present invention as described above for the conversion of I to II.

For compound VI where $R=$bromine or iodine and $R''=H$, treatment with a chlorinating agent such as thionyl chloride and a suitable base such as pyridine or DMAP in a chlorinated solvent at temperatures ranging from 0° C. to 23° C. gives the halo derivative VIII. Treatment of VIII with an alkali metal salt of a heterocycle prepared as described above gives the alkylation product VII. The biaryl derivatives of the present invention are prepared from VII as described above and depicted in Scheme I for the conversion of I to II.

Alternatively, compounds of the present invention wherein $R^1=CN_4H$ can be prepared from VII, $R'''=$bromine or iodine by treatment with 2-triphenylmethyltetrazoyl phenyl boronic acid in the presence of a suitable base such as sodium carbonate, sodium hydroxide or potassium carbonate and a suitable palladium catalyst, preferably $Pd(PPh_3)_4$, in a suitable solvent mixture such as toluene, ethanol and water at temperatures ranging from 50° C. to 110° C. to give V wherein $R'=CN_4C(C_6H_5)_3$, Removal of the triphenylmethyl protecting group in an alcoholic solvent such as methanol or ethanol gives compounds of the present invention.

For compounds of the present invention wherein $X^{14}=N$, the halide VIII, wherein $R=$bromide, is prepared from the 5-bromopyrindane VI' by a two step procedure: (i) oxidation of the pyridyl nitrogen with a suitable agent such as m-chloroperbenzoic acid in a suitable solvent such as chloroform at temperatures ranging from 23° C. to the reflux temperature of the solvent; and (ii) a one pot rearrangement and chlorination with a suitable agent such as phosphorous oxychloride in the presence of a base such as triethylamine.

Compounds of the present invention wherein W is a naphthyl ring are prepared by the route illustrated in Scheme III. The appropriately substituted amine VIII is generally first deprotonated with a base MH where M is lithium, sodium or potassium in a suitable solvent such as DMF, DMSO or THF, and then treated with the appropriately substituted 2-chloro-2-nitropyridine IX (prepared as described by known literature procedures and also described in EP-400974-A, published Dec. 5, 1990) at temperatures ranging from 23° C. to the reflux temperature of the solvent. The coupled product X can be reduced preferably with $H_2$ and palladium on activated carbon (Pd/C) in a solvent mixture such as ethyl acetate (EtOAc) and ethanol (EtOH) under high pressure preferably 45 psi. Condensation of the diamine XI with the appropriate carboxylic acid in the presence of an acid such a polyphosphoric acid (PPA) at temperatures ranging from 50° C. to 100° C. gives the heterocyclic derivative XII. Treatment of the XII, R=bromine or iodine with hexaalkylditin and a palladium catalyst (preferably $PdCl_2(PPh_3)_2$) gives the alkyl stannane derivative which can be cross-coupled with a 2-haloaryl derivative using a palladium catalyst (preferably $PdCl_2(PPh_3)_2$) in a solvent such as DMF, dioxane or DME at a temperature between 50°–110° C. to give XIII. In cases where R=OH, compound XII is first treated with triflic anhydride and a base (preferably pyridine or triethylamine) in a chlorinated solvent such as methylene chloride, followed by treatment with LiCl, hexaalkylditin and a palladium catalyst (preferably $PdCl_2(PPh_3)_2$ gives the desired stannane which can be converted to compound XIII as described above. The conversion of XIII, R'=CN, $CO_2CH_3$ or $SO_2NHC(C_6H_5)$ to compounds of the present invention wherein $R^1=CN_4H$, $CO_2H$, or $SO_2NHCOR$ is the same as that described for the conversion of compound V to compounds of the present invention.

The preparation of other compounds of the present invention not specifically described in the foregoing experimental section can be accomplished using combinations of the reactions described above that will be apparent to those skilled in the art.

In each of the reactions discussed or illustrated in Schemes I to III above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula Ar—W—Het and their pharmaceutically acceptable salts (referred to, collectively, herein as "the compounds of the present invention") are useful as angiotensin II antagonists, i.e., they possess the ability to antagonize the effects of angiotensin II at its receptor site in mammals, and therefore they are able to function as therapeutic agents in the treatment of the aforementioned disorders and diseases in an afflicted mammal.

The compounds of the present invention which are basic in nature are capable of forming a wide variety of different salts with various inorganic and organic acids. Although such salts must be pharmaceutically acceptable for administration to animals, it is often desirable in practice to initially isolate a compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of the present invention and their pharmaceutically acceptable salts exhibit angiotensin II receptor-binding activity and therefore are of value in the treatment and prevention of a wide variety of clinical conditions the treatment or prevention of which are effected or facilitated by a decrease in angiotensin II mediated neurotransmission. Such conditions include hypertension, glaucoma, renal disease, congestive heart failure, and cognitive dysfunction. Hence, these compounds are readily adapted to therapeutic use as angiotensin II antagonists for the control and/or treatment of any of the aforesaid clinical conditions in mammals, including humans.

The compounds of the present invention are readily adapted to clinical use as antagonists of angiotensin II at the angiotensin II receptor. The ability of the compounds to antagonize angiotensin II action may be determined by an in vitro angiotensin II rat liver binding assay which measures their ability to displace $^{125}I$ sarcosine-1, isoleucine-8, angiotensin II (SARILE angiotensin II, obtained from New England Nuclear) from rat liver angiotensin II receptors. For this assay, the following materials are used: (1) Homogenation buffer (10 millimoles (mM) Tris, 0.2 moles (M) sucrose, 1.0 mM ethylenediaminetetraacetic acid (EDTA)), prepared using 1.21 grams Tris base, 6.84 grams sucrose and 336 milligrams (rag) EDTA in 1000 milliliters (ml) water, adjusted to pH 7.4 using HCl; (2) Buffer A (50 mM Tris, 5 mM $MgCl_2$), prepared using 6.05 grams Tris base and 1.02 grams magnesium chloride hexahydrate ($MgCl_2 \cdot 6H_2O$) in 1000 ml water; and (3) Assay buffer, prepared using 200 ml Buffer A and 0.5 grams bovine serum albumin (BSA).

In this procedure, male Sprague-Dawley rats are sacrificed by decapitation and the livers are removed quickly and placed in ice cold homogenation buffer (all the following procedures, unless otherwise indicated, are performed at 4° C.). The liver is minced with scissors and homogenized in a chilled ground glass homogenizer at approximately 10 ml buffer/1 gram liver (wet weight). The homogenate is centrifuged at 3000 grams (5000 rotations per minute (rpm), SM24 rotor) for 10 minutes, then the supernatant is centrifuged at 10,000 grams for 13 minutes. The resulting supernatant is then centrifuged at 100,000 grams for one hour. The pellet is resuspended in buffer A to an approximate concentration of 1 ml protein/ml. A BioRad protein assay using Coomassie blue dye is then run. The membrane preparation is aliquoted, frozen and stored at −20° C. On the day of the assay, the preparation is diluted with assay buffer to a final concentration of 600 micrograms ($\mu g$)/ml or with buffer A to a final concentration of 200 $\mu g$/ml. Due to the fact that some compounds of the invention bind to proteins, the use of BSA may interfere with some tests. Accordingly, the assay may be run with or without BSA.

The compound being tested is made up to an initial concentration of 2 mM in 100% DMSO. Dilutions are then made using 10% DMSO in assay buffer or buffer A. Radiolabelled (hot) SARILE angiotensin II is made up at 0.5 nM concentration in assay buffer or 1.0 nM concentration in buffer A. Non-radiolabelled (cold) SARILE angiotensin II is made up at 20 $\mu M$ in 10% DMSO in assay buffer or buffer A for non-specific binding. Using microtitre plates, each incubate receives: 50 $\mu l$ hot SARILE angiotensin II; 50 $\mu l$ membrane preparation; and 100 $\mu l$ buffer (total), cold SARILE angiotensin II (nonspecific binding) or compound to be tested. Each plate consists of the following in triplicate: total binding; nonspecific binding; and varying concentration of compound. Plates are incubated at room temperature for 40 minutes for assays containing BSA or for 120 minutes for assays without BSA, on a rocker plate at high speed. Plates are then aspirated using an Inotech cell harvester. The filters are cut, placed in test tubes and counted on a Gamma Counter. The mean for all triplicate points are calculated and total specific binding is calculated by subtracting nonspecific counts from total counts. Binding in the presence of compound (COUNTS)is calculated by subtracting nonspecific counts from counts in the presence of compound. Percent binding of SARILE angiotensin II in the presence of compound is calculated by dividing COUNTS by total specific counts. Percent inhibition is (1 percent binding) * 100. $IC_{50}$ values (concentration of compound which inhibits binding by 50%)is read from a plot of percent inhibition (linear scale) versus compound concentration (log scale). The compounds of the present invention were found to have $IC_{50}$ values at or less than $10^{-5}M$.

The ability of the compounds of the invention to lower blood pressure in mammals was determined by the following in vivo protocol. Sprague-Dawley rats are placed on a low sodium diet (Purina Labs, 0.07% sodium) for 15 days. On days 11 and 13 of this period, the rats are given furosemide (Lasix, 8 mg/kilogram (kg), i.m.). On day 13, the animals are anesthetized with a pentobarbital-chloral hydrate mixture (30 mg/kg pentobarbital sodium and 10 mg/kg chloral hydrate, i.p.) and the carotid artery and jugular vein are cannulated using PE50 tubing (Clay-Adams). After a 24 hour recovery period, the animals are injected on day 14 with Lasix (10 mg/kg, i.m.) and are placed in plexiglass chambers for blood pressure recording. After dosing rats by either the oral or parenteral routes with the compound being tested, blood pressure is monitored for 5 hours and is displayed on a polygraph. When possible, blood pressure is also checked after 24 hours. According to this protocol, the compounds of the invention are effective in lowering mean arterial pressure at oral dosages from about 0.1 mg/kg to about 30 mg/kg, and at parenteral dosages from about 0.01 mg/kg to about 10 mg/kg, often with a duration of action of greater than 24 hours.

For treatment of the various conditions described above, the compounds of the invention and their pharmaceutically acceptable salts can be administered to the patient either alone or, preferably, in combination with pharmaceutically acceptable carriers or diluents in a pharmaceutical composition according to standard pharmaceutical practice. Such administration may be carried out in single or multiple doses. A compound can be administered via a variety of conventional routes of administration including orally, parenterally, by inhalation, and topically. When the compounds are administered orally, the dose range will generally be from about 0.1 to about 50 mg/kg/day, based on the body weight of the subject to be treated, preferably from about 1 to about 10 mg/kg/day in single or divided doses. If parenteral administration is desired, then an effective dose will generally be from about 0.01 to about 10 mg/kg/day. In some instances it may be necessary to use dosages outside these limits, since the dosage will necessarily vary according to the species, age, weight, and response of the individual patient, severity of the patient's symptoms, potency of the particular compound being administered, type of pharmaceutical formulation chosen, and time period and interval at which administration is carried out.

The compounds of the invention and their pharmaceutically acceptable salts can be administered in a wide variety of different dosage forms, such as in the form of tablets, powders, lozenges, troches, hard candies, sprays, creams, salves, suppositories, jellies, gels, pastes, lotions, ointments, syrups or capsules, aqueous solutions or suspensions, injectable solutions, elixirs, and the like. Such carriers include solid diluents or fillers, sterile aqueous media and various non-toxic organic solvents, etc. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered (preferably pH greater than 8) if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically and this may preferably be done by way of creams, jellies, gels, pastes, ointments and the like, in accordance with standard pharmaceutical practice.

The present invention is illustrated by the following Examples. It will be understood, however, that the invention is not limited to the specific details of these examples. In the following Examples, proton nuclear magnetic resonance ($^1H$ NMR) spectra were measured at 250 or 300 MHz unless otherwise indicated and peak positions are expressed in parts per million (ppm) downfield from tetramethylsilane. The peak shapes are denoted as follows: s, singlet; d, doublet; t, triplet; q, quartet; m, mutiplet; br, broad.

EXAMPLE 1

2-Butyl-5-chloro-1-{5-[2-(1H-tetrazol-5-yl)-phenyl]-indan-1-yl}-1H-imidazole-4-carboxylic acid

A. 5-Tributylstannanyl-indan-1-one

To a mixture of 5-bromo-indan-1-one (2.35 grams, 11.14 millimoles (mmol)) and hexabutylditin (5.60 grams, 11.14 mmol)in DMF 15 mL was added PdCl$_2$(PPh$_3$)$_2$ (772 mg, 1.1 mmol). The reaction mixture was heated at 110° C. for 20 hours. After cooling to room temperature, the reaction mixture was diluted with ethyl acetate (250 mL), filtered through celite and washed with saturated aqueous sodium bicarbonate (NaHCO$_3$) (2×50 mL) and saturated aqueous sodium chloride (NaCl). The ethyl acetate solution was dried (MgSO$_4$) and concentrated in vacuo. The crude residue was chromatographed on SiO$_2$-gel using a gradient of 100% hexanes to 30% ethyl acetate/hexanes to give 2.2 grams of a colorless oil. $^1$H NMR (250 MHz, CDCl$_3$): d 7.70 (d, 1 H), 7.60 (s, 1 H), 7.48 (d, 1 H), 3.15 (t, 2 H), 2.65 (t, 2 H), 1.60 (t, 6 H), 135 (m, 6 H), 0.85 (t, 9 H).

B. 2-(1-Oxo-indan-5-yl)-benzonitrile

A mixture of 5-tributylstannanyl-indan-1-one (2.25 grams, 5.8 mmol), 2-bromobenzonitrile (1.06 grams, 5.8 mmol) and PdCl$_2$(PPh$_3$)$_2$ (421 mg, 0.6 mmol) was heated in dioxane (15 mL) for 20 hours. The reaction was cooled to room temperature, concentrated in vacuo and transferred to a SiO$_2$-gel column. Flash chromatography using a gradient of 25% ethyl acetate/hexanes to 50% ethyl acetate/hexanes yielded 725 mg of a colorless solid. $^1$H NMR (250 MHz, CDCl$_3$): d 7.9 (d, 1 H), 7.8 (d, 1 H), 7.69 (m, 2 H), 7.54 (m, 3 H), 3.24 (t, 2 H), 2.78 (t, 2 H).

C. 2-(1-Hydroxy-indan-5-yl)-benzonitrile

Sodium borohydride (1.03 grams, 27 mmol) was added to a mixture of 2-(1-oxo-indan-5-yl)-benzonitrile (3.2 grams, 13.6 mmol) in methanol (MeOH) (130 mL) at ) 0° C. The reaction mixture was allowed to warm to room temperature and was stirred for 3 hours. After cooling to 0° C., the reaction mixture was quenched with saturated aqueous ammonium chloride (NH$_4$Cl) (25 mL). EtOAc (500 mL) was added and the organic layer was separated and washed with saturated aqueous NaCl (3×100 mL), dried (Na$_2$SO$_4$) and concentrated in vacuo to yield 2.9 grams of a brown oil. $^1$H NMR (250 MHz, CDCl$_3$): d 7.78 (d, 1 H), 7.65 (t, 1 H), 7.50 (m, 5 H), 5.32 (t, 1 H), 3.15 (m, 1 H), 2.92 (m, 1 H), 2.55 (m, 1 H), 2.0 (m, 1 H).

D. 2-(1-Chloro-indan-5-yl)-benzonitrile

To a solution of 2-(1-hydroxy-indan-5-yl)-benzonitrile (3.3 grams, 14 mmol) and pyridine ( 2.4 mL, 30 mmol)in CH$_2$Cl$_2$(30 mL) at 0° C. was added thionyl chloride (3.3 grams, 2.04 mL, 28 mmol). The reaction mixture was allowed to warm slowly to room temperature. After 1 hour, the reaction mixture was cooled to 0° C., quenched with saturated aqueous NaHCO$_3$ (10 mL) and diluted with methylene chloride (CH$_2$Cl$_2$) (100 mL). The organic layer was separated and washed with saturated aqueous NaHCO$_3$ (1×25 mL) and saturated aqueous NaCl (1×25 mL), dried (MgSO$_4$) and concentrated in vacuo to give a yellow oil. $^1$H NMR (250 MHz, CDCl$_3$): d 7.78 (1H, d), 7.65 (1H, t), 7.48 (m, 5 H), 5.48 (dd, 1 H), 3.25 (m, 1 H), 2.98 (m, 1 H), 2.67 (m, 1 H), 2.45 (m, 1 H).

E. 2-Butyl-5-chloro-1-[5-(2-cyano-phenyl)-indan-1-yl]-1H-imidazole-4-carboxylic acid ethyl ester Sodium hydride (40 mg, 1.73 mmol) was added to (2-butyl-5-chloro-1H-imidazol-4-yl)-methanol (400 mg, 1.73 mmol)in 1,4-dioxane (2 mL) at room temperature. After 1 hour, a solution of 2-(1-chloro-indan-5-yl)-benzonitrile (406 mg, 1.73 mmol)in 1,4-dioxane (2 mL) was added. The reaction was heated under reflux for 17 hours, cooled to room temperature and concentrated in vacuo. Chromatography on silicon oxide gel (SiO$_2$-gel) using 30% ethyl acetate/hexanes yielded 177 mg of a colorless oil. $^1$H NMR (250 MHz, d$_6$-DMSO): d 7.95 (1H, d), 7.75 (1H, t), 7.54 (m, 3 H), 7.40 (m, 1 H), 7.1 (m, 1 H), 4.2 (q, 2 H), 3.15 (m), 2.75 (m), 1.65 (m), 1.40 (m), 1.22 (t, 3 H), 0.92 (t, 3 H).

F. 2-Butyl-5-chloro-1-{5-[2-(1H-tetrazol-5-yl)-phenyl]-indan-1-yl}-1H-imidazole-4-carboxylic acid ethyl ester A mixture of 2-butyl-5-chloro-1-[5-(2-cyano-phenyl)-indan-1-yl]-1H-imidazole-4-carboxylic acid ethyl ester (177 mg, 0.41 mmol) and trimethyltin azide (108 mg, 0.5 mmol) was heated in toluene (1.0 mL)for 72 hours. The reaction mixture was cooled to room temperature and concentrated in vacuo. The residue was chromatographed on SiO$_2$-gel using a gradient of 2% MeOH/CH$_2$Cl$_2$ to 15% MeOH/CH$_2$Cl$_2$ to give 50 mg of a colorless oil.

G. 2-Butyl-5-chloro-1-{5-[2-(1H-tetrazol-5-yl)-phenyl]-indan-1-yl}-1H-imidazole-4-carboxylic acid To a solution of 2-butyl-5-chloro-1-{5-[2-(1H-tetrazol-5-yl)-phenyl]-indan -1-yl}-1H-imidazole-4-carboxylic acid ethyl ester (50 mg, 0.1 mmol)in ethanol (2 mL) was added 2N sodium hydroxide (NaOH) (0.5 mL). The reaction mixture was stirred for 20 hours, and then concentrated in vacuo. The residue was diluted with saturated aqueous NaCl (10 mL) and neutralized with concentrated acetic acid (HOAc). The aqueous solution was extracted with chloroform (CHCl$_3$) (3×10 mL). The combined organic extracts were dried (MgSO$_4$) and concentrated in vacuo. The residue was dissolved in EtOAc (0.5 mL) and hexanes were added to precipitate the product. The solid was filtered and dried in vacuo. $^1$H NMR (250 MHz, d$_6$-DMSO): d 7.62 (m, 5 H), 7.08 (s, t), 6.85 (m, 2 H), 6.15 (m, 1 H), 3.1–2.0 (m), 165 (m, 2 H), 140 (m, 2 H), 0.95 (t, 3 H).

EXAMPLE 2

2-Butyl-3-{5-[2-(1H-tetrazol-5-yl)-phenyl]-indan-1-yl}-1,3-diaza-spiro[4.4]-non-1-en-4-one

A. 2-[1-(2-Butyl4-oxo-1,3-diaza-spiro[4.4]non-1-en-3-yl)-indan-5-yl]-benzonitrile Sodium hydride (53 mg, 2.3 mmol) was added to 2-butyl-1,3-diaza-spiro[4.4]non-1-en-4-one (458 mg, 2.36 mmol) in anhydrous 1,4-dioxane (3 mL). After 0.25 hour, a solution of 2-(1-chloro-indan-5-yl)-benzonitrile (300 mg, 1.18 mmol)in dioxane (1.0 mL) was added. The reaction mixture was heated at 110° C. for 20 hours, cooled to room temperature and concentrated in vacuo. The crude residue was chromatographed on SiO$_2$-gel using 50% ethyl acetate/hexanes to give 150 mg of a colorless oil. $^1$H NMR (250 MHz, CDCl$_3$): d 7.80 (d, 1

H), 7.65 (q, 1 H), 7.48 (m, 4 H), 7.10 (d, 1 H), 5.75 (m, 1 H), 3.42 (m), 3.15 (m), 2.85 (m), 2.55 (m), 2.40–1.60 (m), 1.40 (m), 0.88 (t, 3 H).

B. 2-Butyl-3-{5-[2-(1H-tetrazol-5-yl)-phenyl]-indan-1-yl}-1,3-diaza-spiro[4.4]non-1-en-4-one A mixture of 2-[1-(2-butyl-4-oxo-1,3-diaza-spiro[4.4]-non-1-en-3-yl)-indan -5yl]-benzonitrile (150 mg, 0.36 mmol) and trimethyltin azide (196 mg, 0.91 mmol) was heated under reflux in xylene (5.0 mL) for 25 hours. The reaction mixture was cooled to room temperature and concentrated in vacuo. The residue was chromatographed on $SiO_2$-gel using a gradient of 2.5% $MeOH/CH_2Cl_2$ to 10% $MeOH/CH_2Cl_2$ to give 51 mg of a colorless oil. The oil was dissolved in EtOAc and hexanes were added to precipitate the product. The white solid was filtered and dried. $^1H$ NMR (250 MHz, $d_4$-MeOH): d 7.58 (m, 2 H), 7.47 (m, 2 H), 7.00 (s, 1 H), 6.85 (s, 2 H), 5.50 (t, 1 H), 2.95 (m, 2 H), 2.35 (m, 4 H), 1.90–1.41 (m), 1.22 (m, 2 H), 0.80 (t, 3 H).

EXAMPLE 3
(2-Butyl-5-chloro-1-{5-[2-(1h-tetrazol-5-yl)-phenyl]-indan-1-yl}-1H-imidazol-4-yl)-methanol

A. 5-Bromo-indan-1-ol

Sodium borohydride (0.891 grams, 23.45 mmol) was added to a mixture of 5-bromo-indan-1-one (2.0g, 9.38 mmol)in MeOH (25 mL) at 0° C. The reaction mixture was allowed to warm to room temperature and was stirred for 3 hours and quenched with saturated aqueous $NH_4Cl$ (25 mL) was added. The reaction mixture was diluted with EtOAc (200 mL). The organic layer was separated and was washed with saturated aqueous NaCl (3×50 mL), dried over sodium sulfate ($Na_2SO_4$) and concentrated in vacuo to yield 2.0 grams of a brown oil. 1H NMR (250 MHz, $CDCl_3$): d 7.26 (m, 3 H), 5.18 (t, 1 H), 3.03 (m, 1 H), 2.80 (m, 1 H), 2.50 (m, 1 H), 193 (m, 1 H).

B. 5-Bromo-1-chloro-indan

To a solution of 5-bromo-indan-1-ol (2.0 grams, 9.38 mmol) and pyridine (1.6 mL, 20 mmol)in $CH_2Cl_2$ (20 mL) at 0° C. was added thionyl chloride (2.2 grams, 1.30 mL, 18.7 mmol). The reaction mixture was allowed to warm slowly to room temperature. After 1 hour, the reaction mixture was cooled to 0° C., quenched with saturated aqueous $NaHCO_3$ (10 mL) and diluted with $CH_2Cl_2$ (100 mL). The organic layer was separated and washed with saturated $NaHCO_3$ (1×25 mL) and saturated aqueous NaCl (1×25 mL), dried over magnesium sulfate ($MgSO_4$) and concentrated in vacuo to give a yellow oil. $^1H$ NMR (250 MHz, $CDCl_3$): d 7.4 (s, 1 H), 7.36 (d, 1 H), 7.20 (d, 1 H), 5.35 (dd, 1 H), 3.15 (m), 2.84 (m), 2.55 (m), 1.83 (m).

C. 1-(5-Bromo-indan-1-yl)-2-butyl-5-chloro-1H-imidazole-4-carboxylic acid ethyl ester Sodium hydride (64 mg, 2.8 mmol) was added to 2-butyl-5-chloro-1H-imidazole-4-carboxylic acid ethyl ester (647 mg, 2.8 mmol) in anhydrous 1,4-dioxane (3 mL). After 0.25 hour, a solution of 5-bromo-1-chloro-indane (696 mg, 3.0 mmol)in dioxane (2.0 mL) was added. The reaction mixture was heated at 110° C. for 20 hours, cooled to room temperature and concentrated in vacuo. The crude residue was chromatographed on $SiO_2$-gel using 50% ethyl acetate/hexanes to give 486 mg of a colorless oil. $^1H$ NMR (250 MHz, $d_6$-DMSO): d 7.55 (s, 1 H), 7.36 (d, 1 H), 6.86 (d, 1 H), 6.10 (t, 1 H), 4.20 (q, 2 H), 3.25–2.65 (m), 1.65 (m, 2 H), 1.35 (m, 2 H), 122 (t,3H), 0.90 (t, 3 H).

D. [1-(5-Bromo-indan-1-yl)-2-butyl-5-chloro-1H-imidazol-4-yl]-methanol

To a solution of 1-(5-bromo-indan-1-yl)-2-butyl-5-chloro-1H-imidazole-4-carboxylic acid ethyl ester (486 mg, 1.13 mmol)in $CH_2Cl_2$ (5.0 mL) at 0° C. was added diisobutylaluminum hydride (Dibal-H) (1M solution in $CH_2Cl_2$, 5.0 mL). The reaction mixture was allowed to warm to room temperature and was stirred for 0.75 hour, carefully quenched with saturated aqueous $NH_4Cl$ (1 mL) and diluted with $CH_2Cl_2$ (100 mL). The organic solution was separated and washed with saturated aqueous $NaHCO_3$ (2×10 mL), saturated aqueous NaCl (2×10 mL), dried ($MgSO_4$) and concentrated in vacuo. The crude residue was chromatographed on $SiO_2$-gel using 100% EtOAC to give 400 mg of a colorless oil. $^1H$ NMR (250 MHz, $d_6$-DMSO): d 7.55 (s, 1 H), 7.36 (d, 1 H), 6.83 (d, 1 H), 5.95 (t, 1 H), 4.85 (bs, 1 H), 4.18 (s, 2 H), 3.05 (m, 2 H), 2.70 (m, 3 H), 2.26 (m, 1 H), 1.64 (m, 2 H), 1.30 (m, 2 H), 0.90 (m, 3 H).

E. (2-Butyl-5-chloro-1-{5-[2-(1-trityl-1H-tetrazol-5-yl)-phenyl]-indan-1-yl}-1H-imidazol-4-yl)-methanol A mixture of [1-(5-bromo-indan-1-yl)-2-butyl-5-chloro-1H-imidazol-4-yl]-methanol (400 mg, 1.0 mmol), 2-triphenylmethyltetrazoylphenyl boronic acid (1.0 grams, 2.31 mmol) and $Pd(PPh_3)_4$ (116 mg, 0.1 mmol)in aq $Na_2CO_3$ (2M solution, 2.3 mL) and 1,4-dioxane (5 mL) was heated at 100° C. under a nitrogen atmosphere for 17 hours. The reaction mixture was cooled to room temperature and diluted with EtOAc (150 mL). The organic layer was separated and washed with saturated aqueous $NaHCO_3$ (15 mL) and saturated aqueous NaCl (15 mL), dried ($MgSO_4$) and concentrated in vacuo. The crude residue was chromatographed on $SiO_2$-gel using a gradient of 50% ethyl acetate/hexanes to 100% ethyl acetate to give 100 mg of a colorless oil. $^1H$ NMR (250 MHz, $d_6$-DMSO): d 7.76 (d, 1 H), 7.60 (m), 7.35 (m), 6.90 (m), 6.72 (d, 1 H), 5.87 (m 1 H), 4.85 (bs, 1 H), 4.18 (s, 2 H), 3.00 (m, 2 H), 2.65 (m, 3 H), 2.18 (m, 1 H), 1.60 (m, 2 H), 1.32 (m, 2 H), 0.85 (m, 3 H).

F. (2-Butyl-5-chloro-1-{5-[2-(1h-tetrazol-5-yl)-phenyl]-indan-1-yl}-1H-imidazol-4-yl)-methanol A solution of (2-butyl-5-chloro-1-{5-[2-(1-trityl-1H-tetrazol-5-yl)-phenyl]-indan-1-yl}-1H-imidazol-4-yl)-methanol (100 mg) in MeOH (10 mL) was heated under reflux for 8 hours. The reaction mixture was cooled to room temperature and concentrated in vacuo. The crude residue was chromatographed on $SiO_2$-gel using a gradient of 2% $MeOH/CH_2Cl_2$ to 15% $MeOH/CH_2Cl_2$ to give 31 mg of a colorless oil. The oil was dissolved in EtOAc (0.5 mL) and hexanes were added to precipitate a solid. The solid was filtered and dried. $^1H$ NMR (250 MHz, $d_6$-DMSO): d 7.67 (d, 1 H), 7.40 (m, 4 H), 7.05 (s, 1 H), 6.90 (d, 1 H), 6.60 (d, 1 H), 5.95 (t, 1 H), 5.85 (bs, 1 H), 4.18 (s, 2 H), 3.50–2.30 (m), 1.54 (m, 2 H), 1.46 (m, 2 H), 0.90 (t, 2 H).

EXAMPLE 4

(R/S)-2-Ethyl-5,7-dimethyl-3-{5-[2-(1H-tetrazol-5-yl)-phenyl]-indan-1-yl}-3H-imidazo[4,5-b]pyridine

A. (R)-2-(1-Hydroxy-indan-5-yl)-benzonitrile

To a solution of 2-(1-oxo-indan-5-yl)-benzonitrile (300 mg, 1.29 mmol) and (S)-(−)-diphenylprolinol-(CBS)-oxazaborolidine (72 mg, 0.26 mmol) in THF (0.8 mL) at 35° C., was added over a 35 minute period a solution of borane/dimethyl sulfide (0.4 mL) in THF (2.0 mL). The reaction mixture was then quenched with $H_2O$ and diluted with EtOAc (30 mL). The organic layer was separated and washed with saturated aqueous NaCl (2×10 mL), dried and concentrated in vacuo. The crude residue was dissolved in EtOAc (20 mL), activated charcoal was added and the mixture was allowed to stand for 1 hour, filtered and concentrated in vacuo. $[\alpha]D = -8.1°$ (c=1, MeOH).

Mosher's acid chloride (17.8 mg, 0.07 mmol) was added to a solution of (R)-2-(1-hydroxy-indan-5-yl)-benzonitrile (10.0 mg, 0.047 mmol) and 4-N,N-dimethylaminopyridine in $CH_2Cl_2$ (1.0 mL) at room temperature. The reaction was stirred for 1 hour, diluted with $CH_2Cl_2$ (20 mL) and washed with 10% HCl (5 mL), saturated aqueous $NaHCO_3$ (5 mL) and saturated aqueous NaCl (5 mL). The organic solution was dried and concentrated in vacuo to give the Mosher's ester of (R)-2-(1-hydroxy-indan-5-yl)-benzonitrile. % ee=94% by $^1H$ NMR

B. (S)-2-(1-Hydroxy-indan-5-yl)-benzonitrile

This compound was prepared by the method described in Example 4A except that the catalyst used was (R)-(+)-diphenylprolinol-(CBS)-oxazaborolidine. $[\alpha]D = +12.8°$ (c=1.11, MeOH); 94% ee determined by $^1H$ NMR spectroscopy of Mosher's ester

C. 2-[1-(2-Ethyl-5,7-dimethyl-imidazo[4,5-b]pyridin-3-yl)-indan-5-yl]-benzonitrile To a solution of triphenylphosphine (393 mg, 1.5 mmol) in toluene was slowly added diethylazadicarboxylate (261 mg, 1.5 mmol). After 1 hour, this solution was added to a mixture of 2-ethyl-5,7-dimethyl-3H-imidazo[4,5-b]pyridine (350 mg, 2.0 mmol) and 2-(1-hydroxy-indan-5-yl)-benzonitrile (246 mmol, 1.01 mmol). The reaction mixture was stirred for 17 hours at room temperature and concentrated in vacuo. The crude residue was chromatographed on $SiO_2$-gel using 30% ethyl acetate/hexanes. The residue was dissolved in $CHCl_3$, hexanes were added to precipitate out a white solid. The mixture was filtered and the filtrate was concentrated in vacuo to give a yellow oil which solidified upon standing.

D. 2-[1-(2-Ethyl-5,7-dimethyl-imidazo[4,5-b]pyridin-3-yl)-indan-5yl]-benzonitrile-(R)-(−)-1,1'-binaphthyl-2,2'-diyl-phosphonic acid salt 2-[1-(2-Ethyl-5,7-dimethyl-imidazo[4,5-b]pyridin-3-yl)-indan-5-yl]-benzonitrile (3.1 mg, 0.008 mmol) was added to (R)-(−)-1,1'-binaphthyl-2,2'-diyl hydrogen phosphate (2.75 mg, 0.008 mmol) in $d_4$-MeOH (1.0 mL). The complex was allowed to stand for 0.5 hour. $^1H$ NMR (250 MHz, $d_4$-MeOH): d 7.80 (d), 7.72 (d), 7.57 (d, 2 H), 7.46 (t, 2 H), 7.18 (m), 7.00 (m), 6.92* (d, 1 H), 6.86* (d, 1 H), 6.39 (t, 1 H), 3.27 (m, 1 H), 2.87 (m, 3 H), 2.60 (m, 1 H), 2.50 (m, 1 H), 2.35* (s, 3 H), 2.33* (s, 3 H), 2.25 (s, 3 H), 1.15 (t, 3 H). Note: starred (*) peaks correspond to peaks from two different diastereomers. (S)-2-[1-(2-Ethyl-5,7-dimethyl-imidazo[4,5-b]pyridin-3yl)-indan-5-yl]-benzonitrile This compound was prepared from the product of Example 4A, by the method described in Example 4C. The %ee of the compound was determined by $^1H$ NMR spectroscopy using a 1:1 complex of (S)-2-[1-(2-ethyl-5,7-dimethyl-imidazo[4,5-b]pyridin-3-yl)-indan-5-yl]-benzonitrile and (R)-(−)-1,1'-binaphthyl-2,2'-diyl hydrogen phosphate in $d_4$-MeOH; %ee=94%; $[\alpha]D = -63.1°$ (c=0.8, MeOH).

F. (R)-2-[1-(2-Ethyl-5,7-dimethyl-imidazo[4,5-b]pyridin-3-yl)-indan-5-yl]-benzonitrile This compound was prepared from the product of Example 4B, by the method described in Example 4C. %ee=94%; $[\alpha]D = 70.1°$ (c=0.5, MeOH)

G. 2-Ethyl-5.7-dimethyl-3-{5-[2-(1H-tetrazol-5-yl)-phenyl]-indan-1-yl}-3H-imidazo[4,5-b]pyridine A mixture of 2-[1-(2-ethyl-5,7-dimethyl-imidazo[4,5-b]pyridin-3-yl)-indan-5-yl]-benzonitrile (100 mg, 0.26 mmol) and trimethyltin azide (110 mg, 0.51 mmol) in xylene (3.0 mL) was heated under reflux for 48 hours. The reaction mixture was cooled to 23° C. and the solvent was removed in vacuo. The crude residue was chromatographed on $SiO_2$-gel using 10% $MeOH/CH_2Cl_2$ to afford 45 mg of the tetrazole, mp-181° C. $^1H$ NMR (250 MHz, $d_6$-DMSO): d 7.64 (m, 1 H), 7.53 (m, 1 H), 7.15 (s, 1 H), 6.91 (s, 1 H), 6.80 (d, 1 H), 6.70 (d, 1 H), 6.48 (m, 1 H), 3.04 (m,2 H), 2.68 (2H, m) 2.49 (s, 3 H), 2.42 (s, 3 H), 1.25 (t, 3 H); MS (M+): 435

H. (S)-2-Ethyl-5,7-dimethyl-3-{5-[2-(1H-tetrazol-5-yl)-phenyl]-indan-1-yl}-3H-imidazo[4.5b]pyridine This compound was prepared from the product of Example 4E, by the method described in Example 4G. $[\alpha]D = -64°$ (c=0.57, MeOH)

I. (R)-2-Ethyl-5,7-dimethyl-3-{5-[2(1H-tetrazol-5-yl)-phenyl]-indan-1-yl}-3H-imidazo[4,5-b]pyridine This compound was prepared from the product of Example 4F, by the method described in Example 4G. $[\alpha]D = +70°$ (c=0.50, MeOH)

EXAMPLE 5

2-Ethyl-7-methyl-3-{5-[2-(1H-tetrazol-5-yl)-phenyl]-indan-1-yl}-3H-imidazo[4,5-b]pyridine This compound was prepared in two steps from 2-ethyl-7-methyl-3H-imidazo[4,5-b]pyridine and 2-(1-hydroxy-indan-5-yl)-benzonitrile, by the methods described in Example 4C and 4G. $^1H$ NMR (250 MHz, $d_4$-MeOH): d 7.98 (d, 1 H), 7.50 (m, 4 H), 7.10 (s, 1 H), 7.0 (d, 1 H), 6.75 (d, 1 H), 6.65 (d, 1 H), 6.35 (t, 1 H), 3.15 (m, 2 H), 300 (m, 2 H), 2.70 (m, 2 H), 2.53 (s, 1 H), 1.25 (t, 3 H)

EXAMPLE 6

5,7-Dimethyl-2-propyl-3-{5-[2-(1H-tetrazol-5-yl)-phenyl]-indan-1-yl}-3H-imidazo[4,5-b]pyridine This compound was prepared in two steps from 5,7-dimethyl-2-propyl-3H-imidazo[4,5-b]pyridine and 2-(1-hydroxy-indan-5-yl)-benzonitrile, by the methods described in Example 4C and 4G. ¹H NMR (250 MHz, d₄-MeOH): d 7.65 (m, 4 H), 7.18 (s, 1 H), 7.00 (s, 1 H), 6.95 (d, 1 H), 6.80 (d, 1 H), 6.50 (t, 1 H), 3.10 (m), 280 (m), 260 (s, 3 H), 2.50 (s, 3 H), 1.80 (m, 2HO, 0.91 (t, 3 H); mp-173° C.

EXAMPLE 7

2-Cyclopropyl-5,7-dimethyl-3-{5-[2-(1H-tetrazol-5-yl)-phenyl]-indan-1-yl}-3H-imidazo[4,5-b]pyridine This compound was prepared in two steps from 2-cyclopropyl-5,7-dimethyl-3H-imidazo[4,5-b]pyridine and 2-(1-hydroxy-indan-5-yl)-benzonitrile, by the methods described in Example 4C and 4G. ¹H NMR (250 MHz, d₄-MeOH): d 7.50 (m, 4 H), 7.06 (s, 1 H), 6.85 (s, 1 H), 6.80 (d, 1 H), 6.75 (d, 1 H), 6.60 (t, 1 H), 3.00 (m), 2.7 (m), 2.55 (m), 2.45 (s, 6 H), 1.45 (m, 1 H), 1.0 (m, 3 H), 0.76 (m, 1 H); mp-162°–165° C.

EXAMPLE 8

2-Butyl-5,7-dimethyl-3-{5-[2-(1H-tetrazol-5-yl)-phenyl]-indan-1 -yl}- 3H-imidazo[4,5-b]pyridine This compound was prepared in two steps from 2-butyl-5,7-dimethyl-3H-imidazo[4,5-b]pyridine and 2-(1-hydroxy-indan-5-yl)-benzonitrile, by the methods described in Example 4C and 4G. ¹H NMR (250 MHz, d₄-MeOH): d 7.65 (m, 2 H), 7.55 (m, 2 H), 7.15 (s, 1 H), 6.95 (s, 1 H), 6.75 (d, 1 H), 6.50 (t, 1 H), 3.10 (m), 2.75 (m), 2.55 (s, 3 H), 2.49 (s, 3 H), 1.70 (m), 1.30 (m, 2 H), 0.90 (t, 3 H).

EXAMPLE 9

2-Butyl-3-{5-[2-(1H-tetrazol-5-yl)-phenyl]-indan-1-yl}-3H-imidazo[4,5-b]pyridine This compound was prepared in two steps from 2-butyl-3H-imidazo[4,5-b]pyridine and 2-(1-hydroxy-indan-5-yl)-benzonitrile, by the methods described in Example 4C and 4G. ¹H NMR (250 MHz, d₄-MeOH): d 8.19 (d, 1 H); 7.95 (d, 1 H); 7.65 (t, 2 H); 7.55 (d, 2 H); 7.25 (dd, 1 H); 7.18 (s, 1 H); 6.86 (d, 1 H); 7.74 (d, 1H); 6.44 (m, 1 H); 3.10 (m); 2.75 (m); 1.76 (m); 1.35 (m); 0.90 (t, 3 H); mp-124°–127° C.

EXAMPLE 10

2-[1-(Ethyl-5,7-dimethyl-imidazo[4,5-b]pyridin-3-yl)-indan-5-yl]-benzoic acid

A. 5-Hydroxy-indan-1 -one

A solution of 5-methoxy-indan-1-one (4.9 grams, 30 mmol)in 1:1 concentrated HBr/HOAc (150 mL) was heated at 112° C. for 28 hours. The reaction was cooled to 23° C. and filtered through celite. The filtrate was diluted with ethyl acetate (1000 mL) and washed with saturated aqueous NaCl (100 mL), saturated aqueous NaHCO₃ (2×100 mL) and with saturated aqueous NaCl (100 mL). The ethyl acetate solution was dried (MgSO₄) and concentrated in vacuo to give 1.6 grams of crude product. ¹H NMR (250 MHz, d₆-DMSO): d 7.45 (d, 1 H), 6.82 (s, 1 H), 6.78 (d, 1 H), 2.95 (t, 2H), 2.55 (t, 2 H).

B. Acetic acid 1-oxo-indan-5-yl ester

To a solution of 5-hydroxy-indan-1-one (1600 mg, 10.8 mmol)in CH₂Cl₂ (20 mL) at 23° C. were added 4-N,N-dimethylaminopyridine (1830 mg, 15 mmol) and acetic anhydride (1500 mg, 1.4 mL, 15 mmol). The reaction mixture was stirred for 25 hours, quenched with 10% hydrochloric acid (HCl) (20 mL) and diluted with CHCl₃ (500 mL). The organic layer was separated and washed with saturated aqueous NaHCO₃ (20 mL), dried (MgSO₄)and concentrated in vacuo. ¹H NMR (250 MHz, CDCl₃): d 7.78 (d, 2 H), 7.21 (s, 1 H), 7.10 (d, 1 H), 3.28 (t, 2 H), 2.75 (t, 2 H), 2.38 (s, 3 H).

C. Acetic acid 1-hydroxy-indan-5-yl ester

To a solution of acetic acid 1-oxo-indan-5-yl ester (2700 mg, 14.2 mmol) in MeOH (20 mL) at 0° C. was added sodium borohydride (760 mg, 20 mmol). The reaction mixture was stirred for 2 hours, quenched with saturated aqueous NH₄Cl (20 mL) and diluted with ethyl acetate (500 mL). The organic solution was washed with saturated aqueous NaHCO₃ (50 mL) and saturated aqueous NaCl (50 mL), dried (Na₂SO₄) and concentrated in vacuo to give 2.3 grams of the desired product. ¹H NMR (250 MHz, CDCl₃): d 7.35 (d, 2 H), 6.90 (m, 2 H), 5.2 (t, 1 H), 3.0 (m, 1 H), 2.8 (m, 1 H), 2.5 (m, 1 H), 2.3 (s, 3 H), 1.95 (1 H, m).

D. Benzoic acid 5-acetoxy-indan-1-yl ester

To a solution of acetic acid 1-hydroxy-indan-5-yl ester (2.3 grams, 11.9 mmol) in CH₂Cl₂ (18 mL) at 0° C. were added 4-N,N-dimethylaminopyridine (2.19 grams, 18 mmol) and benzoic anhydride (4.1 grams, 18 mmol). The reaction mixture was allowed to warm to 23° C. and was stirred for 17 hours, quenched with 10% HCl (25 mL) and diluted with CHCl₃. The organic layer was separated and washed with saturated aqueous NaHCO₃ (50 mL), dried (MgSO₄) and concentrated in vacuo. The crude residue was chromatographed on SiO₂-gel using 20% ethyl acetate/hexanes to afford the desired product. ¹H NMR (250 MHz, CDCl₃): d 8.05 (d, 2 H), 7.50 (m, 4 H), 7.00 (s, 1 H), 6.95 (d, 1 H), 6.40 (dd, 1 H), 3.2 (m, 1 H), 2.95 (m, 1 H), 2.30 (s, 3 H), 2.25 (m, 1 H).

E. 1-(2-Ethyl,5,7-dimethyl-imidazo[4,5-b]pyridin-3-yl)-indan-5-ol

To a solution of 2-ethyl-5,7-dimethyl-imidazo[4,5-b]pyridine (1100 mg, 6.28 mmol) in DMF (6.0 mL) at 23° C. was added sodium hydride (144 mg, 6.28 mmol). The reaction mixture was stirred for 0.25 hour, then was cooled to 0° C. A solution of the benzoic acid 5-acetoxy-indan-1-yl ester (930 mg, 3.14 mmol) in DMF (2.0 mL) was added dropwise. The reaction mixture was allowed to warm to 23° C. and was stirred for 25 hours, quenched with saturated NaHCO₃ (20 mL) and diluted with EtOAc (100 mL). The organic solution was washed with saturated aqueous NaCl (20 mL), dried (MgSO₄) and concentrated in vacuo. The crude residue was chromatographed on SiO₂-gel using 75% ethyl acetate/hexanes to give 1000 mg of a mixture of aryl benzoates and acetates. The mixture of the aryl esters (1000 mg) was dissolved in ethanol (10 ml) at 23° C. and 2N NaOH (5 mL) was added. The reaction mixture was stirred for 20 hours, concentrated in vacuo and diluted with saturated aqueous NaCl (30 mL). The aqueous solution was neutralized with neat acetic acid and extracted with CHCl₃ (3×100 mL). The combined extracts were dried (MgSO$_4$) and concentrated in vacuo to give the desired product. $^1$H NMR (300 MHz, CDCl$_3$): d 6.9 (s, 1 H), 6.7 (s, 1 H), 6.65 (d, 1 H), 6.47 (d, 1 H), 3.2 (m, 1 H), 2.75 (m, 1 H), 2.60 (s, 3H, 2.55 (s, 3 H), 2.45 (m,1 H), 1.2 (t, 3 H).

F. Trifluoromethanesulfonic acid 1-(2-ethyl-5,7-dimethyl-imidazo[4,5-b]pyridin-3-yl)-indan-5-yl ester To a solution of 1-(2-ethyl-5,7-dimethyl-imidazo[4,5-b]pyridin-3-yl)-indan-5-ol (720 mg, 2.33 mmol)in CH$_2$Cl$_2$ (5 mL) at −78° C. were added pyridine (237 mg, 0.24 mL, 3 mmol) and triflic anhydride (818 mg, 0.48 mL, 2.9 mmol). The reaction mixture was stirred at −78° C. for 0.5 hour and at 0° C. for 1 hour and was quenched with saturated aqueous NaHCO$_3$ (5 mL). The organic layer was separated and washed with saturated aqueous NaCl (5 mL), dried MgSO$_4$) and concentrated in vacuo. $^1$H NMR (250 MHz, CDCl$_3$): d 7.06 (dd, 1 H), 6.95 (d,s 2 H), 6.87 (s, 1 H), 6.46 (1H, m), 3.48 (m, 1 H), 3.12 (q, 2 H), 2.85 (m, 2 H), 2.65 (m, 1 H), 2.61 (s, 3 H), 2.50 (s, 3 H), 1.28 (t, 3 H).

G. 2-Ethyl-5,7-dimethyl-3(5-tributylstannanyl-indan-1-yl)-3H-imidazo[4,5-b]pyridine To a solution of trifluoromethanesulfonic acid 1-(2-ethyl-5,7-dimethyl-imidazo[4,5-b]pyridin-3-yl)-indan-5-yl ester (1000 mg, 2.27 mmol)in dioxane (5.0 mL) at 23° C. was added hexabutylditin (1.32 grams, 1.13 mL, 2.6 mmol), PdCl$_2$(PPh$_3$)$_3$ (254 mg, 0.22 mmol) and anhydrous lithium chloride (LiCl) (289 mg, 6.8 mmol). The reaction mixture was heated under a nitrogen (N$_2$) atmosphere at 110° C. for 20 hours. After cooling to 23° C., the solvent was removed in vacuo and the residue was chromatographed on SiO$_2$-gel using 30% ethyl acetate/hexanes to give 520 mg of the desired product. $^1$H NMR (250 MHz, CDCl$_3$): d 7.45 (s, 1 H), 7.21 (d, 2 H), 6.95 (m, 2 H), 6.6 (m, 1 H), 3.2 (m, 2 H), 2.80 (m, 1 H), 2.65 (s, 3 H), 2.55 (s, 3 H), 2.45 (m, 1 H), 1.75–0.7 (m, 30 H).

H. 2-[1-(Ethyl-5,7-dimethyl-imidazo[4,5-b]pyridin-3-yl)-indan-5-yl]-benzoic acid methyl ester A mixture of 2-ethyl-5,7-dimethyl-3-(5-tributylstannyl-indan-1-yl)-3H-imidazol[4,5-b]pyridine (224 mg, 0.41 mmol), methyl 2-iodobenzoate (131 mg, 0.5 mmol) and PdCl$_2$(PPh$_3$)$_2$ (28 mg, 0.04 mmol) was heated in anhydrous 1,4-dioxane for 20 hours. After cooling to room temperature, the reaction mixture was concentrated in vacuo and chromatographed on SiO$_2$-gel using a gradient of 30% EtOAc/hexanes to 50% EtOAc/hexanes to give 50 mg of a colorless oil. $^1$H NMR (250 MHz, CDCl$_3$): d 7.80 (1 H, d), 7.55 (t, 1 H), 7.43 (t, 2 H), 7.30 (s, 1 H), 7.10 (d, 2 H), 6.90 (m, 2 H), 6.52 (m, 1H), 3.30 (m, 1 H), 3.15 (m, 1 H), 2.85 (q, 2 H), 2.65 (s, 3 H), 2.57 (s, 3 H), 0.90 (t, 3H.

I. 2-[1-(2-Ethyl-5,7-dimethyl-imidazo[4,5-b]pyridin-3-yl)-indan-5-yl]-benzoic acid To a mixture of 2-[1-ethyl-5,7-dimethyl-imidazo[4,5-b]pyridin-3-yl)-indan-5-yl]-benzoic acid methyl ester (50 mg, 0.12 mmol)in EtOH (3.0 ml) was added 2N NaOH (1.0 ml). The reaction mixture was heated at 60° C. for 1 hour, and was then allowed to stir at 23° for 17 hours, concentrated in vacuo and neutralized with HOAc (3 drops). The aqueous residue was extracted with CHCl$_3$ (3×20 ml), dried and concentrated in vacuo. The residue was azeotroped with heptane to give 22 mg of a colorless solid, mp-199°–201° C. $^1$H NMR (250 MHz, d$_6$-DMSO): d 7.72 (d, 1 H), 7.60 (d, 1 H), 7.55 (d, 1 H), 7.50 (d, 1 H), 7.45 (s, 1 H), 7.10 (d, 1 H), 6.92 (s, 1 H), 6.85 (d, 1 H), 6.45 (t, 1 H), 3.10 (m, 2 H), 2.70 (m, 2 H), 2.60 (m, 2 H), 2.50 (s, 3 H), 2.45 (s, 3 H), 1.25 (t, 3 H).

EXAMPLE 11

2-[5-(2-Ethyl-5,7-dimethyl-imidazo[4,5-b]pyridin-3-yl)-5,6,7,8-tetrahydro-naphthalen-2-yl]-benzoic acid

A. 6-Hydroxy-3,4-dihydro-2H-naphthalen-1-one

This compound was prepared from 6-methoxy-tetralone, by the method described in Example 10A. $^1$H NMR (250 MHz, CDCl$_3$): d 8.0 (d, 1 H), 6.77 (dd, 1 H), 6.70 (d, 1 H), 2.91 (t, 1 H), 2.65 (t, 1 H), 2.10 (m, 1 H).

B. Acetic acid 5-oxo-5,6,7,8-tetrahydro-4H-naphthalen-2-yl ester

This compound was prepared from the product of Example 11A, by the method described in 10B. $^1$H NMR (250 MHz, CDCl$_3$): d 8.1 (d, 1 H), 7.0 (m), 3.0 (m, 2 H), 2.56 (m, 1 H), 2.36 (s, 3 H), 2.20 (m, 1 H), 1.90 (m, 1 H). C. Acetic acid 5-hydroxy-5,6,7,8-tetrahydro-4H-naphthalen-2-yl ester This compound was prepared from the product of Example 11 B, by the method described in Example 10C. $^1$H NMR (250 MHz, CDCl$_3$): d 7.48 (d, 1 H), 6.93 (dd, 1 H), 6.84 (s, 1 H), 4.78 (t, 1 H), 2.78 (m), 2.30 (s, 3 H), 1.90 (m). D. Benzoic acid 6-acetoxy-1,2,3,4-tetrahydro-naphthalen-1-yl ester This compound was prepared from the product of Example 11 C, by the method described in Example 10D. $^1$H NMR (250 MHz, CDCl$_3$): d 8.03 (d, 2 H), 7.5 (m, 4 H), 6.89 (m, 2 H), 6.24 (t, 1 H), 2.85 (m, 2 H), 2.30 (s, 3 H), 2.10 (m, 3 H), 1.92 (m, 1 H).

E. 5-(2-Ethyl-5,7-dimethyl-imidazo[4,5-b]pyridin-3-yl)-5.6,7,8-tetrahydro-4H-naphthalen-2-ol This compound was prepared from the product of Example 11D, by the method described in Example 10E. $^1$H NMR (250 MHz, CDCl$_3$): d 6.92 (s, 1 H), 6.45 (bs, 1 H), 6.14 (m, 3 H), 2.95 (m), 2.70 (m), 2.63 (s, 3 H), 2.57 (s, 3 H), 2.46 (m), 2.25 (m), 2.08 (m), 190 (m), 1.18 (t, 3 H).

F. Trifluoromethane sulfonic acid 5-(2-ethyl-5,7-dimethyl-imidazo[4,5-b]pyridin-3-yl)-5,6,7,8-tetrahydro-4H-naphthalen-2-yl ester This compound was prepared from the product of Example 11 E, by the method described in Example 10F. $^1$H NMR (250 MHz, CDCl$_3$): d 7.12 (s, 1 H), 6.89 (m, 2HO, 6.63 (d, 1 H), 6.27 (t, 3 H), 3.02 (m), 2.65 (s, 3 H), 2.55 (s, 3 H), 2.45 (m), 233 (m), 2.15 (m), 1.26 (t, 3 H).

G. 2-Ethyl-5,7-dimethyl-3-(6-tributylstannanyl-1,2,3,4-tetrahydro-4H-naphthalen-1-yl)-3H-imidazo[4,5-b]pyridine This compound was prepared from the product of Example 11 F, by the method described in Example 10G. $^1$H NMR (250 MHz, CDCl$_3$): d 7.25 (s, 1 H), 7.05 (d, 1 H), 6.88 (s, 1 H), 6.48 (d, 1 H), 6.36 (m, 1 H), 2.93

(m), 2.65 (s, 3 H), 2.55 (s, 3 H), 2.35 (m), 2.12 (m), 1.60–1.00 (m), 0.85 (t, 3 H).

H. 2-[5-(2-Ethyl-5,7-dimethyl-imidazo[4,5-b]pyridin-3-yl)-5,6,7,8-tetrahydro-naphthalen-2-yl]-benzoic acid methyl ester This compound was prepared from the product of Example 11 G, by the method described in Example 10H. $^1$H NMR (250 MHz, CDCl$_3$): d 7.79 (d, 1 H), 7.52 (m, 1 H), 7.40 (m, 1 H), 7.19 (s, 1 H), 6.94 (d, 1 H), 6.92 (s, 1 H), 6.59 (d, 1 H), 6.31 (t, 1 H), 3.64 (s, 3 H), 2.99 (m, 1 H), 2.65 (s, 3 H), 2.59 (s, 3 H), 2.49 (m, 1 H), 2.34 (m, 1 H), 2.14 (m, 2 H), 1.24 (t, 3 H).

I. 2-[5-(2-Ethyl-5,7-dimethyl-imidazo[4,5-b]pyridin-3-yl)-5,6,7,8-tetrahydro-naphthalen-2-yl]-benzoic acid This compound was prepared from the product of Example 11H, by the method described in Example 10 I. $^1$H NMR (250 MHz, d$_6$-DMSO): d 7.79 (d, 1 H), 7.55 (t, 1 H), 7.45 (d, 1 H), 7,36 (d, 1 H), 7.20 (s, 1 H), 6.98 (d, 1 H), 6.92 (s, 1 H), 6.35 (d, 1 H), 6.10 (m, 1 H), 2.90 (m), 2.70 (m), 2.45 (s, 6 H), 2.10 (m), 1.18 (t, 3 H).

EXAMPLE 12

2-[5-(2-Ethyl-5,7-dimethyl-imidazo[4,5-b]pyridin-3-yl)-6,7,8,9-tetrahydro-5H-benzocyclohepten-2-yl]-benzonitrile

A. Acetic acid 5-oxo-6,7,8,9-tetrahydro-5H-benzocyclohepten-2-yl ester

This compound was prepared from 7-hydroxy-benzosuberone, by the method described in Example 1OB. 1H NMR (250 MHz, CDCl$_3$): d 7.80 (d, 1 H), 7.04 (dd, 1 H), 6.95 (d, 1 H), 2.91 (t, 2 H), 2.72 (t, 2 H), 2,30 (s, 3 H), 1.85 (m, 4 H).

B. Acetic acid 5-hydroxy-6,7,8,9-tetrahydro-5H-benzocyclohepten-2-yl ester

This compound was prepared from the product of Example 12A, by the method described in Example 10C. 1H NMR (250 MHz, CDCl$_3$): d 7.44 (d, 1 H), 6.90 (dd, 1 H), 6.82 (d, 1 H), 4.90 (t, 1 H), 2.90 (dd, 1 H), 2.70 (dd, 1 H), 2.30 (s, 3 H), 2.10–1.50 (m, 6 H).

C. Benzoic acid 2-acetoxy-6,7,8,9-tetrahydro-5H-benzocyclo-hepten-5-yl ester This compound was prepared from the product of Example 12B, by the method described in Example 10D. $^1$H NMR (250 MHz, CDCl$_3$): d 8.15 (d, 2 H), 7.50 (m), 7.01 (d, 1 H), 6.89 (m, 2 H), 6.22 (t, 1 H), 3.07 (m, 1 H), 2.78 (m, 1 H), 2.31 (s, 3 H), 2.12 (m, 2 H), 1.95 (m, 2 H) 1.75 (m, 2 H).

D. 5-(2-Ethyl-5,7-dimethyl-imidazo[4,5-b]pyridin-3-yl)-6,7,8,9-tetrahydro-5H-benzocyclohepten-2-ol This compound was prepared from the product of Example 12C, by the method described in Example 10E. $^1$H NMR (250 MHz, CDCl$_3$): d 6.90 (s, 2 H), 6.10 (d, 1 H), 6.00 (bs, 1 H), 5.85 (d, 1 H), 2.9 (m), 2.69 (s, 3 H), 2.60 (s, 3 H), 2.55–1.75 (m), 1.40 (t, 3 H).

E. Trifluoromethane sulfonic acid 5-(2-ethyl-5,7-dimethyl-imidazo[4,5-b]pyridin-3-yl)-6,7,8,9-tetrahydro-5H-benzocyclo-hepten-2-yl ester This compound was prepared from the product of Example 12D, by the method described in Example 10F. $^1$H NMR (250 MHz, CDCl$_3$): d 7.14 (s, 1 H), 6.95 (s, 1 H), 6.87 (dd, 1 H), 5.93 (bs, 1 H), 3.06 (m), 2.92 (m), 2.68 (m), 2.68 (s, 3 H), 2.55 (s, 3 H), 2.4–1.75 (m), 1.39 (m), 0.86 (t, 3 H).

F. 2-Ethyl-5,7-dimethyl-3-(2-tributylstannanyl-6,7,8,9-tetrahydro-5H-benzocyclohepten-5-yl)-3H-imidazo[4,5-b]pyridine This compound was prepared from the product of Example 12E, by the method described in Example 1OG. $^1$H NMR (250 MHz, d$_6$-DMSO): d 7.28 (s, 1 H), 7.05 (d, 1 H), 6.94 (s, 1 H), 5.95 (d, 1 H), 5.90 (bs, 1 H), 2.85 (m), 2.70 (m), 2.50 (s, 3 H), 2.44 (s, 3 H), 2.25 (m), 2.00 (m), 1.60 (m), 1.50 (m), 1.40 (m), 1.10 (m), 1.00 (m), 0.85 (m).

G. 2-[5-(2-Ethyl-5,7-dimethyl-imidazo[4,5-b]pyridin-3-yl)-6,7,8,9-tetrahydro-5H-benzocyclohepten-2-yl]-benzonitrile This compound was prepared from the product of Example 12F, by the method described in Example 10H using 2-bromobenzonitrile. $^1$H NMR (250 MHz, CDCl$_3$): d 7.73 (dd, 1H, J=1.10, 7.67Hz), 7.60 (dd, 1H, J=1.18, 7.60Hz), 7.42 (m), 7.13 (dd, 1H, J=1.79, 8.00Hz), 6.88 (s, 1 H), 6.41 (d, 1H, J=8.0Hz), 6.00 (bs, 1 H), 3.05 (m), 2.92 (q, 2 H), 2.68 (s, 3 H), 2.55 (s, 3 H), 2.42–1.81 (m), 1.65 (m), 1.36 (m), 0.94 (t, 3 H); IR (cm$^{-1}$): 2224.

EXAMPLE 13

2-[1-(2-Ethyl-5,7-dimethyl-imidazo[4,5-b]pyridin-3-yl)-indan-5-yl]-benzonitrile

To a solution of 2-ethyl-5,7-dimethyl-3-(5-tributyl-stannanyl-indan-1-yl)-3H-imidazo[4,5-b]pyridine (264 mg, 0.48 mmol) in anhydrous dioxane (1.5 mL) was added 2-bromobenzonitrile (109 mg, 0.6 mmol) and PdCl$_2$(PPh$_3$)$_2$ (34 mg, 0.048 mmol). The reaction mixture was heated under reflux for 17 hours, cooled to 23° C. and concentrated in vacuo. The crude residue was chromatographed on SiO$_2$-gel using 30% ethyl acetate/hexanes to give 100 mg of the desired product. $^1$H NMR (250 MHz, CDCl$_3$): d 7.75 (1H, m), 7.64 (1H, m), 7.55 (m, 2 H), 7.35 (t, 1 H), 7.00 (d, 1 H), 6.9 (s, 1 H), 6.6 (m, 1 H), 3.4 (m, 2 H), 2.95 (m, 1 H), 2.65 (s, 3 H), 2.58 (s, 3 H), 1.3 (t, 3 H).

EXAMPLE 14

2-Ethyl-5,7-dimethyl-3-{6-[2-(1H-tetrazol-5-yl)-phenyl]-1,2.3,4-tetrahydro-naphthalen-1-yl}-3H-imidazo[4,5-b]pyridine

A. 2-[5-(2-Ethyl-5,7-dimethyl-imidazo[4,5-b]pyridin-3-yl)-5,6,7,8-tetrahydro-4H-naphthalen-2-yl]-benzonitrile This compound was prepared from the product of Example 11G, by the method described in Example 13. $^1$H NMR (250 MHz, d$_6$-DMSO): d 7.58 (t, 2 H), 7.47 (t, 2 H), 7.00 (s, 1 H), 6.95 (s, 2 H), 6.70 (d, 1 H), 6.20 (d, 1

H), 6.05 (bs, 1 H), 3.40 (bs, 1H), 3.05–2.00 (m), 2.51 (s, 3 H), 2.45 (s, 3 H), 1.15 (t, 3 H).

B.
2-Ethyl-5,7-dimethyl-3-{6-[2-(1H-tetrazol-5-yl)-phenyl]-1,2,3,4-tetrahydro-naphthalen-1-yl}-3H-imidazo[4,5-b]pyridine This compound was prepared from the product of Example 14A, by the method described in Example 4G. $^1$H NMR (250 MHz, CDCl$_3$): d 7.75 (d, 1 H), 7.63 (m, 1 H), 7.47 (m, 3 H), 7.17 (d, 1 H), 6.85 (s, 1 H), 6.67 (s, 1 H), 6.30 (t, 1 H), 3.12–1.82 (m), 2.67 (s, 3 H), 2.57 (s, 3 H), 0.90 (t, 3 H).

EXAMPLE 15

2-Ethyl-5,7-dimethyl-3-{2-[2-(1H-tetrazol-5-yl)-phenyl]-6,7,8,9-tetrahydro-5H-benzocyclohepten-5-yl}-3H-imidazo[4,5-b]pyridine This compound was prepared from the product of Example 12G, by the method described in Example 4G. $^1$H NMR (250 MHz, d$_4$-MeOH): d 7.62 (d, 2 H), 7.53 (d, 2 H), 7.00 (s, 1 H), 6.90 (s, 1 H), 6.78 (d, 1 H), 6.10 (d, 1 H), 6.00 (bs, 5 H), 2.61 (s, 3 H), 2.50 (s, 3 H), 2.39–1.85 (m), 1.40 (m), 1.30 (t, 3 H).

EXAMPLE 16

2-Ethyl-5,7-dimethyl-3-{7-[2-(1H-tetrazol-5-yl)-phenyl]-chroman-4-yl}-3H-imidazo[4,5-b]pyridine $^1$H NMR (250 MHz, d$_6$-DMSO): d 7.60 (m, 4 H), 6.91 (s, 1 H), 6.66 (s, 1 H), 6.37 (d, J=7.8 Hz, 1 H), 6.25 (d, J=7.8 Hz, 1 H), 4.46 (m, 2 H), 2.72 (bs, 1 H) 2.49 (s, 3 H), 2.48 (m, 2 H), 2.43 (s, 3 H), 2.29 (m, 1 H), 1.24 (m, 4 H); mp-220°–221° C.; Anal. calc. for C$_{26}$H$_{25}$N$_7$O: C, 69.15; H, 5.58; N, 21.71; found: C, 68.93; H, 5.67; N, 21.65.

EXAMPLE 17

2-Ethyl-5,7-dimethyl-3-{3-[2-(1H-tetrazol-5-yl)-phenyl]-6,7-dihydro-5H-[1]pyrindin-7-yl}-3H-imidazo[4,5-b]pyridine

A. 3-Bromo-6,7-dihydro-5H-[1]pyrindine

To a solution of 6,7-dihydro-5H-[1]pyrindine (20 gm) and AlCl$_3$ (56 gm) at 100° C. was added 10 mL of bromine over 2 hours, stirred an additional 15 minutes, cooled to room temperature, and poured over ice. The pH of the reaction was adjusted until it was basic with NaOH and then celite and ether were added and the mixture filtered. The filter cake was washed well with additional ether and the filtrate was extracted from the aqueous layer. The ether layer was washed with saturated aqueous NaCl solution, dried over MgSO$_4$, filtered, and concentrated to dryness. The residue was chromatographed on silica gel using 10:1 hexane/ethyl acetate as the eluant to yield 4 gm of compound. $^1$H NMR (CDCl$_3$): d 8.35 (s, 1 H), 7.60 (s, 1 H), 2.90 (m, 4 H), 2.10 (m, 2 H).

B. 3-Bromo-6,7-dihydro-5H-[1]pyrindine N-Oxide

A solution of 3-bromo-6,7-dihydro-5H-[1]pyrindine (4 gm) and 3-chloroperoxybenzoic acid (2 equiv.) in CHCl$_3$ was refluxed for 3 hours. An additional equivalent of 3-chloroperoxybenzoic acid was added to the reaction and heating was continued for another hour. The reaction was then cooled to 0° C., filtered, and extracted into CH$_2$Cl$_2$ from 1:1 saturated NaHCO$_3$/-NaHCO$_3$ (using caution), dried over Na$_2$SO$_4$, filtered, and evaporated. The residue was chromatographed on silica gel using 10:1 hexane/ethyl acetate to remove remaining starting material, ethyl acetate to remove 3-chloroperoxybenzoic acid residues, and then 10% MeOH/CH$_2$Cl$_2$ to elute the final compound. The product yield was 2 gm. $^1$H NMR(CDCl$_3$): d 8.20 (s, 1 H), 7.25 (s, 1 H), 3.10 (m, 4 H), 2.20 (m, 2 H).

C. 3-Bromo-7-chloro-6,7-dihydro-5H-[1]pyrindine

To a solution of 3-bromo-6,7-dihydro-5H-[1]pyridine N-Oxide (250 mg, 1.17 mM) in 3 mL of CH$_2$Cl$_2$ at room temperature was added POCl$_3$ (0.131 mL, 1.4 mM) and triethylamine (0.202 mL, 1.4 mM). The reaction was stirred at room temperature for 2 hours then was extracted from saturated NaHCO$_3$ solution into ethyl acetate, washed with saturated NaCl, dried over MgSO$_4$, filtered, and concentrated to dryness. The product was used crude in the next step. $^1$H NMR (CDCl$_3$): d 8.60 (s, 1 H), 7.80 (s, 1 H), 5.40 (d, 1 H), 3.00 (m, 2 H), 2.20 (m, 2 H)

D. 3-(3-Bromo-6,7-dihydro-5H-[1]pyrindin-7-yl)-2-ethyl-5,7-dimethyl-3H-imidazo[4,5-b]pyridine To a solution of NaH, 60% in oil, (163 mg) in 3 mL of 1,4-dioxane was added 2-ethyl-5,7-dimethyl-3H-imidazo[4,5-b]pyridine (1.1 gm) at room temperature and stirred for 30 minutes. Then 3-bromo-7-chloro-6,7-dihydro-5H-[1]pyrindine (500 mg, 2.15 mM) in 2 mL of 1,4-dioxane and anhydrous NaBr (442 mg) were added to the solution and the reaction was heated to 100° C. for 24 hours. The reaction was then cooled to room temperature, concentrated to dryness, and extracted into ethyl acetate from water. The organic layers were dried over MgSO$_4$, filtered, and evaporated to dryness. The residue was purified by chromatography on silica gel to yield 110 mg of product.

E.
2-Ethyl-5,7-dimethyl-3-{3-[2-(1-trityl-1H-tetrazol-5-yl)-phenyl]-6,7-dihydro-5H-[1]pyrindin-7-yl}-3H-imidazo[4,5-b]pyridine To a solution of 3-(3-bromo-6,7-dihydro-5H-[1]pyrindin-7-yl)-2-ethyl-5,7-dimethyl-3H-imidazo[4,5-b]pyridine (110 mg, 0.296 mM), Pd(PPh$_3$)$_4$ (17 mg, 0.015 mM) and 2M Na$_2$CO$_3$ (0.444 mL) in 0.888 mL of DME at reflux added 2-(1-triphenylmethyltetrazoyl)phenyl boronic acid (512 mg, 1.18 mM). The reaction was heated at reflux for 6 hours, then an additional 2 equivalents of 2-(1-triphenylmethyltetrazoyl)phenyl boronic acid and 5% of Pd(PPh$_3$)$_4$ was added and heating was continued for 16 hours. The reaction was then cooled to room temperature, evaporated to dryness, and extracted into ethyl acetate. The organic layer was dried over MgSO$_4$, filtered, concentrated to dryness, and chromatographed on silica gel using 8:1 to 2:1 hexane/ether as the gradient eluant to yield 49 mg of compound. $^1$H NMR (CDCl$_3$): d 8.15 (s, 1 H), 8.00 (t, 1 H), 7.40 (bm, 14 H), 6.95 (m, 6 H), 4.15 (q, 2 H), 3.20 (m, 2 H), 2.70 (m, 3 H), 2.60 (s, 3 H), 2.45 (s, 3 H), 1.30 (t, 3 H).

F.
2-Ethyl-5,7-dimethyl-3-{3-[2-(1H-tetrazol-5-yl)-phenyl]-6,7-dihydro-5H-[1]-7-yl}-3H-imidazo[4,5-b]pyridine A solution of 2-ethyl-5,7-dimethyl-3-{3-[2-(1-trityl-1H-tetrazol-5-yl)-phenyl]-6,7-dihydro-5H-[1]pyrindin-7-yl}-3H-imidazo[4,5-b]pyridine (49.9 mg) in 3 mL of MeOH was heated to reflux for 3 hours, cooled to room temperature, and concentrated to dryness. The residue was chromatographed on silica gel using 2% MeOH/CH$_2$Cl$_2$ to 5% MeOH/1% HOAc/CH$_2$Cl$_2$ as the gradient eluant. The compound was then crystallized from ethyl acetate to yield 6 mg of product. $^1$H NMR (d$_4$-MeOH): d 8.00 (s, 1 H), 7.60 (m, 5 H), 6.90 (s, 1 H), 4.10 (q, 2 H), 3.10 (m, 2 H), 2.75 (m, 3 H), 2.55 (s, 3 H), 2.40 (s, 3 H), 1.35 (t, 3 H).

EXAMPLE 18

2-[5-(2-Butyl-imidazo[4,5-b]pyridin-3,-yl)-naphthalen-2-yl]-benzoic acid

A. N-(6-Benzyloxy-naphthalen-1-yl)-acetamide

A mixture of N-(6-hydroxy-naphthalen-1-yl)-acetamide (5.72 grams, 28 mmol), benzyl bromide (4.78 grams, 28 mmol) and potassium carbonate (4.14 grams, 30 mmol) in DMF (50 mL) was stirred at room temperature for 20 hours. The reaction was diluted with ether (250 mL) and was washed with saturated aqueous NaHCO$_3$ (2×30 mL) and saturated aqueous NaCl (2×30 mL), dried MgSO$_4$) and concentrated in vacuo. The crude residue was azeotroped with heptane (2×100 mL) to give a colored solid. The solid was filtered and washed with hexanes to give 5.0 grams of a colorless product. $^1$ NMR (250 MHz, CDCl$_3$): d 7.25 (m, 11 H), 4.4 (s, 2 H), 2.16 (s, 3 H).

B. 6-Benzyloxy-naphthalen-1 -ylamine

A solution of N-(6-benzyloxy-naphthalen-1-yl)-acetamide (5.0 grams, 17 mmol) and potassium hydroxide (2.88 grams, 51 mmol) in EtOH (35 mL)/H$_2$O (25 mL) was heated at 93° C. for 17 hours. After cooling to room temperature, the reaction mixture was concentrated in vacuo. The residue was diluted with saturated aqueous NaCl (25 mL) and extracted with EtOAc (5×100 mL). The combined organic extracts were dried over MgSO$_4$ and concentrated in vacuo. The crude residue was chromatographed on SiO$_2$-gel using 30% ethyl acetate/hexanes. $^1$H NMR (250 MHz, CDCl$_3$): d 7.78 (d, 1 H), 7.50 (s, 1 H), 7.38 (m, 3 H), 7.20 (m, 4 H), 6.67 (d, 1 H), 5.18 (s, 2 H).

C. (6-Benzyloxy-naphthalen-1-yl)-(3-nitro-pyridin-2-yl)-amine

To a solution of 6-benzyloxy-naphthalen-1-ylamine (4.71 grams, 16.2 mmol) in DMF (25.0 mL) at room temperature was added NaH (372 mg, 16.2 mmol). After 0.5 h, 2-chloro-3-nitropyridine (5.53 grams, 35 mmol) and potassium iodide (2.8 grams, 17 mmol) were added. The reaction mixture was heated at 146° C. for 17 hours. The cooled solution was diluted with ether (300 mL) and the ether solution was washed with saturated aqueous NaCl (2×50 mL). The aqueous solution was extracted with CHCl$_3$ (3×50 mL). The combined extracts were dried (MgSO$_4$) and concentrated in vacuo. The crude residue was chromatographed on SiO$_2$-gel using a gradient of 20% ethyl acetate/hexanes to 50% ethyl acetate/hexanes to 3.0 grams of a yellow product. $^1$H NMR (250 MHz, CDCl$_3$): d 8.63 (dd, 1H, J=1.65, 4.8 Hz), 8.58 (dd, 1H, J=1.7, 8.3 Hz), 8.41 (dd, 1H, J=1.73, 4.43 Hz), 8.23 (dd, 1H, J=1.63, 10.2 Hz), 7.93 (d, 1H, J=10 Hz), 7.75 (d, 1H, J=7.32 Hz), 7.68 (d, 1H, J=8.1 Hz), 7.26 (m, 6 H), 6.80 (dd, 1H, J=4.4, 8.1 Hz), 5.25 (s, 2 H).

D. 2-(6-Benzyloxy-naphthalen-1-yl)-pyridine-2,3-diamine

A solution of (6-benzyloxy-naphthalen-1-yl)-(3-nitro-pyridin-2-yl)-amine (3.0 g) in EtOH (150 mL) was added to a mixture of Pd/C (700 mg)in EtOH (30 mL). The reaction mixture was hydrogenated on a paar shaker at 45 psi for 17 hours. The reaction mixture was filtered through celite and concentrated in vacuo. The residue was azeotroped with heptane (200 mL). $^1$H NMR (250 MHz, d$_6$-DMSO): d 8.75 (d, 1 H), 8.51 (s, 1 H), 7.95 (m, 2 H), 7.82 (m, 1 H), 7.40 (m), 7.18 (dd, 1 H), 7.09 (m, 1 H), 6.54 (dd, 1 H), 5.25 (s, 2 H).

E. 3-(Benzyloxy-naphthalen-1-yl)-2-butyl-3H-imidazo[4,5-b]pyridine

A solution of 2-(6-benzyloxy-naphthalen-1-yl)-pyridine-2,3-diamine (3.0 grams, 7.83 mmol) in valeric anhydride (5 mL) was heated at 175° C. for 3 hours. The reaction mixture was cooled to room temperature and diluted with EtOH (100 mL). 2N NaOH (50 mL) was added and the reaction mixture was stirred for 2 hours and concentrated in vacuo. The residue was diluted with saturated aqueous NaCl (25 mL) and the solution was extracted with CHCl$_3$ (3×100 mL). The combined extracts were dried and concentrated in vacuo. The residue was chromatographed on SiO$_2$-gel using a gradient of 50% ethyl acetate/hexanes to 100% ethyl acetate. $^1$H NMR (250 MHz, CDCl$_3$): d 8.26 (d, 1 H), 8.08 (d, 1 H), 7.92 (d, 1 H), 7.78 (dd, 1 H), 7.59 (t, 1 H), 7.42 (m), 7.27 (dd, 1 H), 7.16 (dd, 1 H), 7.08 (s, 1 H), 7.01 (dd, 1 H), 5.22 (s, 2 H), 2.64 (t, 2 H), 1.72 (m, 2 H), 1.28 (m, 2 H), 0.84 (t, 3 H).

F. 5-(2-Butyl-imidazo[4,5-b]pyridin-3-yl)-naphthalen-2-ol

A solution of 3-(benzyloxy-naphthalen-1-yl)-2-butyl-3H-imidazo[4,5-b]-pyridine (1500 g) in EtOH (75 mL) was added to a mixture of Pd/C (3.56 g) in EtOH (50 mL). The mixture was hydrogenated on a paar shaker at 50 psi for 72 hours. The reaction mixture was filtered through celite and concentrated in vacuo to give 1.13 grams of an amorphous solid. $^1$H NMR (250 MHz, CDCl$_3$): d 8.48 (d, 1 H), 8.24 (d, 1 H), 7.52 (m), 7.37 (dd, 1 H), 7.26 (d, 2 H), 6.68 (dd, 2 H), 6.60 (s, 1 H), 2.67 (t, 2 H), 170 (m, 2 H), 1.23 (m, 2 H), 0.78 (t, 3 H).

G. Trifluoromethanesulfonic acid 5-(2-butyl-imidazo[4,5-b]pyridin-3-yl)-naphthalen-2-yl ester To a solution of 5-(2-butyl-imidazo[4,5-b]pyridin-3-yl)-naphthalen-2-ol (1130 mg, 3.58 mmol) in CH$_2$Cl$_2$ (8 mL) at −78° C. were added pyridine (316 mg, 0.32 mL, 4.0 mmol) and triflic anhydride (1128 mg, 0.673 mL, 4.0 mmol). The reaction mixture was stirred at −78° C. for 0.5 hour and at −30° C. for 1.5 hours, then was quenched with saturated aqueous NaHCO$_3$ (5 mL). The aqueous solution was extracted with CHCl$_3$ (50 mL) and the organic solution was dried (MgSO$_4$) and concentrated in vacuo. $^1$H NMR (250 MHz, CDCl$_3$): d 8.25 (d, 1 H), 8.10 (t, 2 H), 7.90 (d, 1 H), 7.76 (t, 1 H), 7.64 (dd, 1 H), 7.26 (m), 2.67 (t, 2 H), 1.75 (m, 2 H), 1.27 (m, 2 H), 0.83 (t, 3 H).

H.

2-Butyl-3-(6-tributylstannanyl-naphthalen-1-yl)-3H-imidazo[4,5-b]pyridine

To a solution of trifluoromethanesulfonic acid 5-(2-butyl-imidazo[4,5-b]-pyridin-3-yl)-naphthalen-2-yl ester (262 mg, 0.58 mmol) in dioxane (1.0 mL) at 23° C. was added hexabutylditin (305 mg, 0.2 mL, 0.6 mmol), PdCl$_2$(PPh$_3$)$_3$ (139 mg, 0.12 mmol) and anhydrous LiCl (75 mg, 1.8 mmol). The reaction mixture was heated under a N$_2$ atmosphere at 110° C. for 20 hours. After cooling to 23° C., the solvent was removed in vacuo and the residue was chromatographed on SiO$_2$-gel using 30% ethyl acetate/hexanes to give 120 mg of the desired product. $^1$H NMR (250 MHz, CDCl$_3$): d 8.39 (d, 1 H), 8.18 (d, 1 H), 8.08 (s, 1 H), 8.04 (d, 1 H), 7.67 (t, 1 H), 7.53 (d, 2 H), 7.30 (dd, 1 H), 7.04 (d, 1 H), 2.69 (m, 2 H), 1.60 (m), 1.3 (m), 1.1 (m), 0.90 (m), 0.78 (t, 3 H).

I.

2-[5-(2-Butyl-imidazo[4,5-b]pyridin-3-yl)-naphthalen-2-yl]-benzoic acid methyl ester A mixture of 2-butyl-3-(6-tributylstannanyl-naphthalen-1-yl)-3H-imidazo[4,5-b]-pyridine (120 mg, 0.22 mmol), methyl 2-iodobenzoate (79 mg, 0.3 mmol) and PdCl$_2$(PPh$_3$)$_2$ (15 mg, 0.02 mmol) in 1.0 mL DMF was heated at 105° C. for 20 hours. The cooled reaction mixture was poured into H$_2$O (20 mL). The aqueous solution was extracted with EtOAc (3×50 mL). The combined extracts were washed with saturated aqueous NaHCO$_3$(25 mL), dried MgSO$_4$) and concentrated in vacuo. The residue was chromatographed on SiO$_2$-gel using a gradient of 20% ethyl acetate/hexanes to 100% ethyl acetate to give 40 mg of product. $^1$H NMR (250 MHz, CDCl$_3$): d 8.27 (dd, 1H, J=1.15, 4.85 Hz), 8.14 (dd, 1H, J=1.21, 7.96 Hz), 8.08 (d, 1H, J=8.2 Hz), 7.94 (d, 1H, J=1.4 Hz), 7.89 (d, 1H, J=7.9 Hz), 7.69 (t, 1 H), 7.58 (m), 7.48 (m), 7.26 (m), 7.14 (d, 1H, J=8.5 Hz), 3.57 (s, 3 H), 2.72 (t, 2 H), 1.78 (m, 2 H), 1.27 (m, 2 H), 0.83 (t, 3 H).

J.

2-[5-(2-Butyl-imidazo[4,5-b]pyridin-3-yl)-naphthalen-2-yl]-benzoic acid

To a solution of 2-[5-(2-butyl-imidazo[4,5-b]pyridin-3-yl)-naphthalen-2-yl]-benzoic acid methyl ester (40 mg) in EtOH (1.0 mL) at room temperature was added 2N NaOH (0.5 mL). The reaction mixture was heated at 50° C. for 17 hours. The cooled solution was concentrated in vacuo. The residue was diluted with saturated aqueous NaCl (10 mL) and neutralized with concentrated HOAc. The aqueous solution was extracted with CHCl$_3$ (3×30 mL). The combined extracts were dried MgSO$_4$) and concentrated in vacuo. The residue was azeotroped with heptane (30 mL) and diluted with EtOAc (1 mL) and hexanes (15 mL). The solid that precipitated was filtered and dried. $^1$H NMR (250 MHz, d$_6$-DMSO): d 8.15 (m, 4 H), 7.72 (m, 3 H), 7.46 (m, 4 H), 7.30 (dd, 1 H), 6.94 (d, 1 H), 2.63 (m, 2 H), 1.63 (m, 2 H), 1.25 (m, 2 H), 0.74 (t, 3 H).

EXAMPLE 19

2-Butyl-3-{6-[2-(1H-tetrazol-5-yl)-phenyl]-naphthalen-1-yl}-3H-imidazo[4,5-b]pyridine

A.

2-[5-(2-Butyl-imidazo[4,5-b]pyridin-3yl)-naphthalen-2-yl]-benzonitrile

To a solution of 2-butyl-3-(6-tributylstannanyl-naphthalen-1-yl)-3H-imidazo[4,5-b]pyridine (310 mg, 0.56 mmol) in anhydrous dioxane (1.5 mL) was added 2-bromobenzonitrile (109 mg, 0.6 mmol) and PdCl$_2$(PPh$_3$)$_3$ (44 mg, 0.06 mmol). The reaction mixture was heated under reflux for 17 hours, cooled to 23° C. and concentrated in vacuo. The crude residue was chromatographed on SiO$_2$-gel using 30% ethyl acetate/hexanes to give 85 mg of the desired product. $^1$H NMR (250 MHz, CDCl$_3$): d 8.28 (d, 1 H), 8.25 (s, 1 H), 8.17 (dd, 2 H), 7.60 (m, 7 H), 7.28 (m, 2.70 (t, 2 H), 1.76 (m, 2 H), 1.32 (m, 2 H), 0.83 (t, 3 H).

B.

2-Butyl-3-{6-[2-(1H-tetrazol-5-yl)-phenyl]-naphthalen-1-yl}-3H-imidazo[4,5-b]pyridine A mixture of 2-[5-(2-butyl-imidazo[4,5-b]pyridin-3-yl)-naphthalen-2-yl]-benzonitrile (85 mg, 0.21 mmol) and trimethyltin azide (108 mg, 0.50 mmol) in xylene (2.5 mL) was heated under reflux for 17 hours. The reaction mixture was cooled to 23° C. and the solvent was removed in vacuo. The crude residue was dissolved in EtOH (5 mL) and 2N NaOH (5 mL) was added. After 0.5 hour, the reaction mixture was concentrated in vacuo. The residue was dissolved in saturated aqueous NaCl (2 mL) and neutralized with concentrated HOAc. The aqueous solution was extracted with CHCl$_3$ (3×10 mL). The combined extracts were dried (MgSO$_4$) and concentrated in vacuo. The residue was azeotroped with heptane, diluted with EtOAc (1 mL) and hexanes (25 mL). The solid that precipitated was filtered and dried. $^1$H NMR (250 MHz, d$_6$-DMSO): d 8.13 (m, 3 H), 7.96 (s, 1 H), 7.65 (m, 6 H), 7.30 (m, 1 H), 7.12 (dd, 1 H), 6.86 (d, 1 H), 2.55 (m, 2 H), 1.63 (m, 2 H), 1.22 (m, 2 H), 0.74 (t, 3 H).

EXAMPLE 20

2-Ethyl-5,7-dimethyl-3-{6-[2-(1H-tetrazol-5-yl)-phenyl]-naphthalen-1-yl}-3H-imidazo[4,5-b]pyridine

A.

(6-Benzyloxy-naphthalen-1-yl)-(4,6-dimethyl-3-nitro-pyridin-2-yl)-amine

This compound was prepared from the product of Example 18B, by the method described in Example 18C using 2-chloro-3-nitro-4,6-dimethyl-pyridine. $^1$H NMR (250 MHz, CDCl$_3$): d 7.90 (t, 2H), 7.60 (d, 1H), 7.45 (m, 6H), 7.25 (m, 2H), 6.55 (s, 1H), 5.20 (s, 2H), 2.60 (s, 3H), 2.35 (s, 3H).

B.

5-(3-Amino-4,6-dimethyl-pyridin-2-ylamino)-naphthalen-2-ol

This compound was prepared from the product of Example 20A, by the method described in Example 18D. $^1$H NMR (250 MHz, d$_4$-MeOH): d 7.75 (d, 1H), 7.50 (d, 1H), 7.30 (t, 1H), 7.20 (s, 1H), 7.10 (d, 1H), 7.00 (d, 1H), 6.65 (s, 1H), 2.35 (s, 3H), 2.20 (s, 3H).

C. 5-(2-Ethyl-5,7-dimethyl-imidazo[4,5-b]pyridin-3-yl)-naphthalen-2-ol

This compound was prepared from the product of Example 20B, by the method described in Example 18E. $^1$H NMR (250 MHz, CDCl$_3$): d 7.75 (s, 1H), 7.60 (d, 1H), 7.50 (t, 1H), 7.35 (s, 1H), 7.00 (d, 1H), 6.80 (d, 1H), 6.60 (d, 1H), 2.76 (s, 3H), 2.75 (q, 2H), 2.50 (s, 3H), 1.55 (t, 3H).

D. Trifluoromethanesulfonic acid 5-(2-ethyl-5,7-dimethyl-imidazo[4,5-b]pyridin-3-yl)-naphthalen-2-yl ester This compound was prepared from the product of Example 20C, by the method described in Example 18G. $^1$H NMR (250 MHz, CDCl$_3$): d 8.15 (d, 1H), 7.90 (d, 1H), 7.80 (t, 1H), 7.55 (d, 1H), 7.35 (d, 1H), 7.05 (s, 1H), 7.00 (s, 1H), 2.75 (s, 3H), 2.45 (q, 2H), 2.20 (s, 3H), 1.30 (t, 3H).

E. 2-Ethyl-5,7-dimethyl-3-{6-[2-(1-trityl-1H-tetrazol-5-yl)-phenyl]-naphthalen-1-yl}-3H-imidazo[4,5-b]pyridine This compound was prepared from the product of Example 20D by the method described in Example 17E. $^1$H NMR (250 MHz, CDCl$_3$): d 8.00 (d, 1H), 7.90 (d, 1H), 7.80 (s, 1H), 7.65 (t, 1H), 7.50 (m, 4H), 7.15 (m, 4H), 7.00 (m, 6H), 6.90 (m, 2H), 6.75 (m, 6H), 2.45 (q, 2H), 2.35 (s, 3H), 2.05 (s, 3H), 1.15 (t, 3H).

F. 2-Ethyl-5,7-dimethyl-3-{6-[2-(1H-tetrazol-5-yl)-phenyl]-naphthalen-1-yl}-3H-[4,5-b]pyridine This product was produced from the product of Example 20E by the method described in Example 17F. $^1$H NMR (250 MHz, d$_4$-MeOH): d 8.00 (d, 1H), 7.80 (s, 1H), 7.60 (m, 6H), 7.10 (d, 1H), 6.95 (s, 1H), 6.85 (d, 1H), 2.60 (s, 3H), 2.55 (q, 2H), 2.30 (s, 3H), 1.10 (t, 3H).

We claim:

1. A compound of the formula:

wherein Ar is selected from the group consisting of

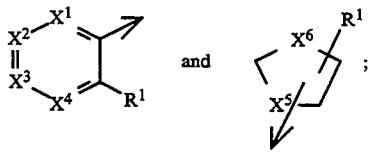

and X$^1$, X$^2$, X$^3$ and X$^4$ are independently selected from CR$^2$ and nitrogen;

one of X$^5$ and X$^6$ is CH and the other is S;

R$^1$ is selected from the group consisting of CO$_2$H, NHSO$_2$CF$_3$, CONHSO$_2$(C$_1$-C$_8$)alkyl, PO$_3$H, SO$_3$H, —CONHSO$_2$(C$_6$H$_5$), CONHSO$_2$CF$_3$, tetrazole,

and —SO$_2$NHCO$_2$(C$_1$-C$_8$)alkyl;

R$^2$ is selected from hydrogen, (C$_1$-C$_8$)alkyl, (C$_2$-C$_{10}$)alkenyl, (C$_3$-C$_8$)cycloalkyl, halo, hydroxy, —O—(C$_1$-C$_6$)alkyl, —S—(C$_1$-C$_6$)alkyl, —SO—(C$_1$-C$_6$)alkyl, —SO$_2$—(C$_1$-C$_6$)alkyl, —NR$^3$R$^4$, and phenyl, wherein said phenyl is optionally mono-, di- or tri-substituted with substituents independently selected from hydrogen, (C$_1$-C$_8$)alkyl, (C$_2$-C$_{10}$)alkenyl, (C$_3$-C$_8$)cycloalkyl, halo, (C$_1$-C$_6$)alkoxy, —S—(C$_1$-C$_6$)alkyl, —SO—(C$_1$-C$_6$)alkyl, —SO$_2$—(C$_1$-C$_6$)alkyl, —O—(C$_1$-C$_6$)alkyl, and —NR$^3$R$^4$;

R$^3$ and R$^4$ are independently selected from hydrogen, (C$_1$-C$_8$)alkyl, (C$_2$-C$_{10}$)alkenyl and (C$_3$-C$_8$)cycloalkyl, or R$^3$ and R$^4$, together with the nitrogen to which they are attached, form a cyclic 5-7 membered saturated or partially saturated carbocyclic or heterocyclic ring with one or two heteroatoms independently selected from nitrogen, oxygen and sulfur; and the dotted line represents that the ring containing X$^5$ and X$^6$ is aromatic;

W is a carbobicyclic or heterobicyclic ring system having the formula

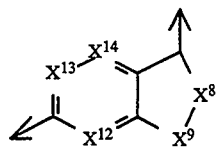

and each of X$^8$ and X$^9$ is independently selected from CHR$^5$, O, S, SO, SO$_2$, and NR$^6$;

X$^{12}$, X$^{13}$, and X$^{14}$ are independently selected from CR$^7$ or N;

R$^5$ is selected from hydrogen, (C$_1$-C$_8$)alkyl, (C$_2$-C$_{10}$)alkenyl, (C$_3$-C$_8$)cycloalkyl, —O—(C$_1$-C$_6$)alkyl, and phenyl, wherein said phenyl is optionally mono-, di- or tri-substituted with substituents independently selected from hydrogen, (C$_1$-C$_8$)alkyl, (C$_2$-C$_{10}$)alkenyl, (C$_3$-C$_8$)cycloalkyl, halo, (C$_1$-C$_6$)alkoxy, —S—(C$_1$-C$_6$)alkyl, —SO—(C$_1$-C$_6$)alkyl, —SO$_2$—(C$_1$-C$_6$)alkyl, —O—(C$_1$-C$_6$)alkyl, and —NR$^3$R$^4$;

R$^6$ is selected from (C$_1$-C$_8$)alkyl, (C$_3$-C$_8$)cycloalkyl and phenyl, wherein said cycloalkyl is saturated or partially saturated and wherein said cycloalkyl may optionally contain a heteroatom selected from nitrogen, oxygen, and sulfur, and said phenyl is optionally mono-, di- or tri-substituted with substituents independently selected from hydrogen, (C$_1$-C$_8$)alkyl, (C$_2$-C$_{10}$)alkenyl, (C$_3$-C$_8$)cycloalkyl, halo, (C$_1$-C$_6$)alkoxy, —S—(C$_1$-C$_6$)alkyl —SO—(C$_1$-C$_6$)alkyl, —SO$_2$—(C$_1$-C$_6$)alkyl, —O—(C$_1$-C$_6$)alkyl, and —NR$^3$R$^4$;

R$^7$ is selected from hydrogen, (C$_1$-C$_8$)alkyl, (C$_2$-C$_{10}$)alkenyl, (C$_3$-C$_8$)cycloalkyl, halo, hydroxy, —O—(C$_1$-C$_6$)alkyl, —S—(C$_1$-C$_6$)alkyl, —SO—(C$_1$-C$_6$)alkyl, —SO$_2$—(C$_1$-C$_6$)alkyl, —NR$^3$R$^4$, and phenyl, wherein said phenyl is optionally mono-, di- or tri-substituted with substituents selected from hydrogen, (C$_1$-C$_8$)alkyl, (C$_2$-C$_{10}$)alkenyl, (C$_3$-C$_8$)cycloalkyl, halo, (C$_1$-C$_6$)alkoxy, —S—(C$_1$-C$_6$)alkyl, —SO—(C$_1$-C$_6$)alkyl, —SO$_2$—(C$_1$-C$_6$)alkyl, —O—(C$_1$-C$_6$)alkyl, and —NR$^3$R$^4$; and Het is selected from the group consisting of:

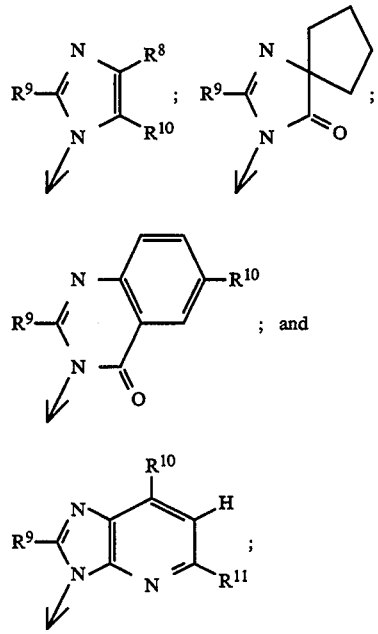

and $R^8$, $R^9$, $R^{10}$ and $R^{11}$ are independently selected from hydrogen, $(C_1-C_8)$alkyl, $(C_2-C_{10})$alkenyl, $(C_3-C_8)$cycloalkyl, halo, $(C_1-C_6)$alkoxy, —S—$(C_1-C_6)$alkyl, —SO—$(C_1-C_6)$alkyl, —$CO_2H$, —$SO_2N_3R^4$, —$NR^3R^4$, and phenyl, wherein said phenyl is optionally mono-, di-, or tri-substituted with halo, hydroxy, nitro, $(C_1-C_8)$alkyl, $(C_3-C_6)$cycloalkyl, $(C_1-C_7)$alkoxy, $(C_1-C_7)$alkylthio, and amino, wherein said amino is optionally mono- or di-substituted with $(C_1-C_7)$alkyl;

and wherein each occurrence of $R^3$ can be the same or different from any other occurrence of $R^3$, and each occurrence of $R^4$ can be the same or different from any other occurrence of $R^4$;

with the proviso that no more than two of $X^1$, $X^2$, $X^3$ and $X^4$ can be nitrogen;

or a pharmaceutically acceptable salt thereof.

2. A compound according to claim 1 selected from the group consisting of:
2-butyl-5-chloro-1-{5-[2-(1H-tetrazol-5-yl)-phenyl]-indan-1-yl}-1H-imidazole-4-carboxylic acid ethyl ester;
2-butyl-5-chloro-1-{5-[2-(1H-tetrazol-5-yl)-phenyl]-indan-1 -yl}-1H-imidazole-4-carboxylic acid;
2-butyl-3-{5-[2-(1H-tetrazol-5-yl)-phenyl]-indan-1-yl}-1,3-diazaspiro[4.4]non-1-en-4-one;
(2-butyl-5-chloro-1-{5-[2-(1H-tetrazol-5-yl)-phenyl]-indan-1-yl}-1H-imidazol-4-yl)-methanol;
2-ethyl-5,7-dimethyl-3-{5-[2-(1H-tetrazol-5-yl)-phenyl}-indan-1-yl}-3H-imidazo[4,5-b]pyridine;
(S)-2-ethyl-5,7-dimethyl-3-{5-[2-(1H-tetrazol-5-yl)-phenyl]-indan-1-yl}-3H-imidazo[4,5-b]pyridine;
(R)-2-ethyl-5,7-dimethyl-3-{5-[2-(1H-tetrazol-5-yl)-phenyl]-indan-1-yl}-3H-imidazo[4,5-b]pyridine;
2-ethyl-7-methyl-3-{5-[2-(1H-tetrazol-5-yl)-phenyl}-indan-1-yl}-3H-imidazo[4,5-b]pyridine;
5,7-dimethyl-2-propyl-3-{5-[2-(1H-tetrazol-5-yl)-phenyl]-indan-1yl}-3H-imidazo[4,5-b]pyridine;
2-cyclopropyl-5,7-dimethyl-3-{5-[2-(1H-tetrazol-5-yl)-phenyl]-indan-1-yl}-3H-imidazo[4,5-b]pyridine;
2-butyl-5,7-dimethyl-3-{5-[2-(1H-tetrazol-5-yl)-phenyl]-indan-1-yl}-3H-imidazo[4,5-b]pyridine;
2-butyl-3-{5-[2-(1H-tetrazol-5-yl)-phenyl]-indan-1-yl}-3H-imidazo[4,5-b]pyridine;
2-[1-(2-ethyl-5,7-dimethyl-imidazo[4,5-b]pyridin-3-yl)-indan-5-yl-benzoic acid.

3. A compound according to claim 1 comprising:
2-ethyl-5,7-dimethyl-3-{3-[2-(1H-tetrazol-5-yl)-phenyl]-6,7-dihydro-5H-[1]pyrindin-7-yl}-3H-imidazo[4,5-b]pyridine.

4. A pharmaceutical composition for treating or preventing a condition selected from the group consisting of hypertension, glaucoma, renal disease, congestive heart failure, and cognitive dysfunction in a mammal, comprising an amount of a compound of claim 1 effective in treating or preventing such condition, and a pharmaceutically acceptable carrier.

5. A method of treating or preventing a condition selected from the group consisting of hypertension, glaucoma, renal disease, congestive heart failure, and cognitive dysfunction in a mammal, comprising administering to said mammal an amount of a compound of claim 1 effective in treating or preventing such condition.

6. A pharmaceutical composition for antagonizing the effects of angiotensin II in a mammal, comprising an angiotensin II antagonizing amount of a compound of claim 1 and a pharmaceutically acceptable carrier.

7. A method of antagonizing the effects of angiotensin II in a mammal, comprising administering to said mammal an angiotensin II antagonizing amount of a compound of claim 1.

8. A pharmaceutical composition for treating or preventing a condition selected from the group consisting of hypertension, glaucoma, renal disease, congestive heart failure, and cognitive dysfunction in a mammal, comprising an amount of a compound of claim 1 effective in antagonizing the effect of angiotensin II at its receptor site, and a pharmaceutically acceptable carrier.

9. A method of treating or preventing a condition selected from the group consisting of hypertension, glaucoma, renal disease, congestive heart failure, and cognitive dysfunction in a mammal, comprising administering to said mammal an amount of a compound of claim 1 effective in antagonizing the effect of angiotensin II at its receptor site.

10. A pharmaceutical composition for treating or preventing a disorder in a mammal, the treatment or prevention of which is effected or facilitated by blocking the action of angiotensin II at its receptor, comprising an amount of a compound of claim 1 effective in antagonizing the effect of angiotensin II at its receptor site, and a pharmaceutically acceptable carrier.

11. A method of treating or preventing a disorder in mammal, the treatment or prevention of which is effected or facilitated by blocking the action of angiotensin II at its receptor, comprising administering to said mammal an amount of a compound of claim 1 effective in antagonizing the effect of angiotensin II at its receptor site.

12. A pharmaceutical composition for treating or preventing a disorder in a mammal, the treatment or prevention of which is effected or facilitated by blocking the action of angiotensin II at its receptor, comprising an amount of a compound of claim 1 effective in treating or preventing such disorder, and a pharmaceutically acceptable carrier.

13. A method of treating or preventing a disorder in mammal, the treatment or prevention of which is effected or facilitated by blocking the action of angiotensin II at its receptor, comprising administering to said mammal an amount of a compound of claim 1 effective in treating or preventing such disorder.

* * * * *